US011794012B2

(12) United States Patent
Napadow et al.

(10) Patent No.: US 11,794,012 B2
(45) Date of Patent: Oct. 24, 2023

(54) SYSTEMS AND METHODS FOR RESPIRATORY-GATED NERVE STIMULATION

(71) Applicant: The General Hospital Corporation, Boston, MA (US)

(72) Inventors: Vitaly Napadow, Boston, MA (US); Jill M. Goldstein, Boston, MA (US); Ronald G. Garcia, Boston, MA (US); Benjamin Pless, Boston, MA (US)

(73) Assignee: The General Hospital Corporation, Boston, MA (US)

(*) Notice: Subject to any disclaimer, the term of this patent is extended or adjusted under 35 U.S.C. 154(b) by 285 days.

(21) Appl. No.: 16/629,395

(22) PCT Filed: Jul. 10, 2018

(86) PCT No.: PCT/US2018/041485
§ 371 (c)(1),
(2) Date: Jan. 8, 2020

(87) PCT Pub. No.: WO2019/014250
PCT Pub. Date: Jan. 17, 2019

(65) Prior Publication Data
US 2020/0139126 A1 May 7, 2020

Related U.S. Application Data

(60) Provisional application No. 62/530,913, filed on Jul. 11, 2017.

(51) Int. Cl.
*A61N 1/36* (2006.01)
*A61N 1/05* (2006.01)

(52) U.S. Cl.
CPC ....... *A61N 1/36053* (2013.01); *A61N 1/0551* (2013.01); *A61N 1/36139* (2013.01); *A61N 1/0502* (2013.01); *A61N 1/36096* (2013.01)

(58) Field of Classification Search
CPC .............. A61N 1/36053; A61N 1/0551; A61N 1/36139; A61N 1/0502; A61N 1/36096; A61N 1/0456; A61N 1/36021
See application file for complete search history.

(56) References Cited

U.S. PATENT DOCUMENTS 6,928,324 B2 * 8/2005 Park .................... A61N 1/36585
607/18
2007/0027496 A1 2/2007 Parnis
(Continued)

OTHER PUBLICATIONS

Grassi G, et al. Sympathetic mechanisms, organ damage, and antihypertensive treatment. Curr Hypertens Rep 2011; 13: 303-308.
(Continued)

*Primary Examiner* — Mark W. Bockelman
(74) *Attorney, Agent, or Firm* — QUARLES & BRADY LLP

(57) ABSTRACT

Systems and methods are provided for neurostimulation timed relative to respiratory activity. Neurostimulation may be delivered to the spinal cord, the vagus nerve, and/or branches of the vagus nerve to provide therapeutic outcomes by controlling or adjusting stimulation based on pulmonary activity. In particular, the systems and methods use a detecting device to detect respiratory activity over time. Specific points in the respiratory signal are identified where central autonomic nuclei may be more receptive to afferent input and a stimulator is instructed to provide neurostimulation to at least one auricular branch of a vagus nerve, or to a cervical branch of the vagus nerve, or to a spinal cord of the subject. In this regard, the neurostimulation is advantageously correlated to the detected respiratory activity providing improved therapeutic outcomes.

8 Claims, 8 Drawing Sheets

(56) References Cited

U.S. PATENT DOCUMENTS

| | | |
|---|---|---|
| 2007/0233192 A1 | 10/2007 | Craig |
| 2008/0086181 A1 | 4/2008 | Amurthur |
| 2012/0035680 A1 | 2/2012 | Napadow |
| 2015/0045848 A1 | 2/2015 | Cho |

OTHER PUBLICATIONS

Halliwill Jr, et al. Peripheral chemoreflex and baroreflex interactions in cardiovascular regulation in humans. J Physiol 2003; 552: 295-302.

He W, et al. Auricular acupuncture and vagal regulation. Evid-Based Complement Altern Med ECAM 2012; 2012: 786839.

Hein E, et al. Auricular transcutaneous electrical nerve stimulation in depressed patients: a randomized controlled pilot study. J Neural Transm Vienna Austria 1996 2013; 120: 821-827.

Holtmann, G., et al. Altered vagal and intestinal mechanosensory function in chronic unexplained dyspepsia. Gut 42, 501-506 (1998).

Hotamisligil, G. S. Inflammation and metabolic disorders. Nature 444, 860-867, doi:10.1038/nature05485 (2006).

Hsu C-C, et al. Evaluation of scalp and auricular acupuncture on EEG, HRV, and PRV. Am J Chin Med 2007; 35: 219-230.

Huang, F. et al. Effect of transcutaneous auricular vagus nerve stimulation on impaired glucose tolerance: a pilot randomized study. BMC complementary and alternative medicine 14, 203, doi:10.1186/1472-6882-14-203 (2014).

Huang, H. et al. Acupuncture at otoacupoint heart for treatment of vascular hypertension. J Tradit Chin Med 12, 133-136 (1992).

International Searching Authority, International Search Report and Written Opinion for application PCT/US2018/041485, dated Nov. 9, 2018.

Irwin RW, et al. Frontiers in therapeutic development of allopregnanolone for Alzheimer's disease and other neurological disorders. Front Cell Neurosci 2014; 8: 203.

Iwase S, et al. Role of sympathetic nerve activity in the process of fainting. Front Physiol 2014; 5: 343.

Kara T, et al. Chemoreflexes—physiology and clinical implications. Acta Physiol Scand 2003; 177: 377-384.

Kasparov, S. et al. Differential effects of angiotensin II in the nucleus tractus solitarii of the rat—plausible neuronal mechanism. J Physiol 521 Pt 1, 227-238 (1999).

Kim, J. et al. The somatosensory link in fibromyalgia: functional connectivity of the primary somatosensory cortex is altered by sustained pain and is associated with clinical/autonomic dysfunction. Arthritis & Rheumatology (Hoboken, N. J.) 67, 1395-1405, doi:10.1002/art.39043 (2015).

Kiyokawa, J., et al. Origin, course and distribution of the nerves to the posterosuperior wall of the external acoustic meatus. Anat Sci Int 89, 238-245, doi:10.1007/s12565-014-0231-4 (2014).

Kleiger RE, et al. Decreased heart rate variability and its association with increased mortality after acute myocardial infarction. Am J Cardiol 1987; 59: 256-262.

Koopman, F. A. et al. Vagus nerve stimulation inhibits cytokine production and attenuates disease severity in rheumatoid arthritis. Proc Natl Acad Sci U S A 113, 8284-8289, doi:10.1073/pnas.1605635113 (2016).

Kraus, T. et al. Bold fMRI deactivation of limbic and temporal brain structures and mood enhancing effect by transcutaneous vagus nerve stimulation. J Neural Transm (Vienna) 114, 1485-1493, doi:10.1007/s00702-007-0755-z (2007).

La Rovere MT, et al. Baroreflex sensitivity and heart-rate variability in prediction of total cardiac mortality after myocardial infarction. ATRAMI (Autonomic Tone and Reflexes After Myocardial Infarction) Investigators. Lancet Lond Engl 1998; 351: 478-484.

Lambert E, et al. Sympathetic dysfunction in vasovagal syncope and the postural orthostatic tachycardia syndrome. Front Physiol 2014; 5: 280.

Lange HW, et al. Depressive symptoms predict recurrence of atrial fibrillation after cardioversion. J Psychosom Res 2007; 63: 509-513.

Li M, et al. Vagal nerve stimulation markedly improves long-term survival after chronic heart failure in rats. Circulation 2004; 109: 120-124.

Li, S. et al. Therapeutic effect of vagus nerve stimulation on depressive-like behavior, hyperglycemia and insulin receptor expression in Zucker fatty rats. PLoS One 9, e112066, doi:10.1371/journal.pone.0112066 (2014).

Li, Y. Sensory signal transduction in the vagal primary afferent neurons. Current medicinal chemistry 14, 2554-2563 (2007).

Lin Z-P, et al. Effects of auricular acupuncture on heart rate, oxygen consumption and blood lactic acid for elite basketball athletes. Am J Chin Med 2011; 39: 1131-1138.

Lomarev M, et al. Vagus nerve stimulation (VNS) synchronized Bold fMRI suggests that VNS in depressed adults has frequency/dose dependent effects. J Psychiatr Res 2002; 36: 219-227.

Malbert, C. H., et al. Obesity-Associated Alterations in Glucose Metabolism Are Reversed by Chronic Bilateral Stimulation of the Abdominal Vagus Nerve. Diabetes 66, 848-857, doi:10.2337/db16-0847 (2017).

Mason JW, et al. Elevation of urinary norepinephrine/cortisol ratio in posttraumatic stress disorder. J Nerv Ment Dis 1988; 176: 498-502.

Mcmenamin, C. A., et al. Inhibitory neurotransmission regulates vagal efferent activity and gastric motility. Experimental biology and medicine (Maywood, N.J.) 241, 1343-1350, doi: 10.1177/1535370216654228 (2016).

Mcteague LM, et al. Aversive imagery in posttraumatic stress disorder: trauma recurrence, comorbidity, and physiological reactivity. Biol Psychiatry 2010; 67: 346-356.

Meijer, A. et al. Prognostic association of depression following myocardial infarction with mortality and cardiovasculai events: a meta-analysis of 25 years of research. Gen Hosp Psychiatry 33, 203-216, doi:10.1016/j.genhosppsych.2011.02.007 (2011).

Miyano, Y. et al. The role of the vagus nerve in the migrating motor complex and ghrelin- and motilininduced gastric contraction in suncus. PLoS One 8, e64777, doi:10.1371/journal.pone.0064777 (2013).

Mostoufi SM, et al. Health and distress predictors of heart rate variability in fibromyalgia and other forms of chronic pain. J Psychosom Res 2012; 72: 39-44.

Neff, R. A., et al. Stimulation of NTS activates NMDA and non-NMDA receptors in rat cardiac vagal neurons in the nucleus ambiguus. Brain Res. 792, 277-282 (1998).

Neff, R. A., et al. Respiratory sinus arrhythmia: endogenous activation of nicotinic receptors mediates respiratory modulation of brainstem cardioinhibitory parasympathetic neurons. Circ. Res. 93, 565-572, doi:10.1161/01.RES.0000090361.45027.5B (2003).

Nemeroff, C. B. et al. VNS therapy in treatment-resistant depression: clinical evidence and putative neurobiological mechanisms. Neuropsychopharmacology 31, 1345-1355, doi:10.1038/sj.npp.1301082 (2006).

Nomura, S. et al. Central distribution of primary afferent fibers in the Arnold's nerve (the auricular branch of the agus nerve): a transganglionic HRP study in the cat. Brain Res. 292, 199-205 (1984).

Noorbakhsh F, et al. Allopregnanolone and neuroinflammation: a focus on multiple sclerosis. Front Cell Neurosci 2014; 8: 134.

Noorbakhsh, F. et al. Impaired neurosteroid synthesis in multiple sclerosis. Brain 134, 2703-2721, doi:10.1093/brain/awr200 (2011).

Nurse CA, et al. Signal processing at mammalian carotid body chemoreceptors. Semin Cell Dev Biol 2013; 24: 22-30.

Ouyang, A. et al. Overview of neurogastroenterology-gastrointestinal motility and functional GI disorders: classification, prevalence, and epidemiology. Gastroenterology clinics of North America 36, 485-498, vii, doi:10.1016/j.gtc.2007.07.009 (2007).

Parati G, et al. The human sympathetic nervous system: its relevance in hypertension and heart failure. Eur Heart J 2012; 33: 1058-1066.

Paton, J. F., et al. Signalling across the blood brain barrier by angiotensin II: novel implications for neurogenic hypertension. Journal of molecular medicine (Berlin, Germany) 86, 705-710, doi:10.1007/s00109-008-0324-4 (2008).

(56) References Cited

OTHER PUBLICATIONS

Pavlov VA, et al. The cholinergic anti-inflammatory pathway. Brain Behav Immun 2005; 19: 493-499.
Pavlov VA, et al. The vagus nerve and the inflammatory reflex-linking immunity and metabolism. Nature reviews. Endocrinology 8, 743-754, doi:10.1038/nrendo.2012.189 (2012).
Peers C, et al. Mechanisms for acute oxygen sensing in the carotid body. Respir Physiol Neurobiol 2010; 174: 292-298.
Pellissier, S., et al. Psychological adjustment and autonomic disturbances in inflammatory bowel diseases and irritable bowel syndrome. Psychoneuroendocrinology 35, 653-662, doi:10.1016/j.psyneuen.2009.10.004 (2010).
Peuker ET, et al. The nerve supply of the human auricle. Clin Anat N Y N 2002; 15: 35-37.
Phillips, M. I. et al. Brain renin angiotensin in disease. Journal of molecular medicine (Berlin, Germany) 86, 715-722, doi:10.1007/s00109-008-0331-5 (2008).
Pittig A, et al. Heart rate and heart rate variability in panic, social anxiety, obsessive-compulsive, and generalized anxiety disorders at baseline and in response to relaxation and hyperventilation. Int J Psychophysiol Off J Int Organ Psychophysiol 2013; 87: 19-27.
Prabhakar NR, et al. Peripheral chemoreceptors in health and disease. J Appl Physiol Bethesda Md 1985 2004; 96: 359-366.
Premchand RK, et al. Autonomic regulation therapy via left or right cervical vagus nerve stimulation in patients with chronic heart failure: results of the ANTHEMHF trial. J Card Fail 2014; 20: 808-816.
Reyes Del Paso GA, et al. Aberrances in Autonomic Cardiovascular Regulation in Fibromyalgia Syndrome and Their Relevance for Clinical Pain Reports: Psychosom Med 2010; 72: 462-470.
Rosas-Ballina M, et al. Cholinergic control of inflammation. J Intern Med 2009; 265: 663-679.
Roth WT, et al. Sympathetic activation in broadly defined generalized anxiety disorder. J Psychiatr Res 2008; 42: 205-212.
Sabbah HN, et al. Vagus nerve stimulation in experimental heart failure. Heart Fail Rev 2011; 16: 171-178.
Sanya EO, et al. Impairment of parasympathetic baroreflex responses in migraine patients. Acta Neurol Scand 2005; 111: 102-107.
Saper CB. The central autonomic nervous system: conscious visceral perception and autonomic pattern generation. Annu Rev Neurosci 2002; 25: 433-469.
Sarvari, M. et al. Menopause leads to elevated expression of macrophage-associated genes in the aging frontal cortex: rat and human studies identify strikingly similar changes. J Neuroinflammation 9, 264, doi:10.1186/1742-2094-9-264 (2012).
Schreihofer, A. M. et al. Baro-activated neurons with pulse-modulated activity in the rat caudal ventrolateral medulla express GAD67 mRNA. J. Neurophysiol. 89, 1265-1277, doi:10.1152/jn.00737.2002 (2003).
Schwartz PJ, et al. Sympathetic-parasympathetic interaction in health and disease: abnormalities and relevance in heart failure. Heart Fail Rev 2011; 16: 101-107.
Sclocco R, et al. Neuroimaging brainstem circuitry supporting cardiovagal response to pain—A combined heart rate variability/ultrahigh field (7T) fMRI study. Phil Trans R Soc A; 374.2067 (2016): 20150189.
Sclocco R, et al. Respiratory-gated auricular vagal afferent nerve stimulation (RAVANS) effects on autonomic butflow in hypertension. In: Engineering in Medicine and Biology Society (EMBC), 2017 39th Annual International Conference of the IEEE, Jeju Island, Korea, Jul. 14, 2017. Conf Proc IEEE Eng Med Biol Soc. 2017: 3130-3133.
Serova, L. I., et al. Modulation of responses to stress by estradiol benzoate and selective estrogen receptor agonists. J. Endocrinol. 205, 253-262, doi:10.1677/JOE-10- 0029 (2010).
Shinlapawittayatorn, K. et al. Vagus nerve stimulation initiated late during ischemia, but not reperfusion, exerts cardioprotection via amelioration of cardiac mitochondrial dysfunction. Heart Rhythm 11, 2278-2287, doi: 10.1016/j.hrthm.2014.08.001 (2014).

Shughrue, P. J., et al. Comparative distribution of estrogen receptor-alpha and -beta mRNA in the rat central nervous system. J. Comp. Neurol. 388, 507-525 (1997).
Spyer KM. Neural organisation and control of the baroreceptor reflex. Rev Physiol Biochem Pharmacol 1981; 88: 24-124.
Stavrakis S, et al. Low-level transcutaneous electrical vagus nerve stimulation suppresses atrial fibrillation. J Am Coll Cardiol 2015; 65: 867-875.
Sternberg EM. Neural regulation of innate immunity: a coordinated nonspecific host response to pathogens. Nat Rev Immunol 2006; 6: 318-328.
Tan G, et al. Heart rate variability (HRV) and posttraumatic stress disorder (PTSD): a pilot study. Appl Psychophysiol Biofeedback 2011; 36: 27-35.
Thayer JF, et al. Inflammation and cardiorespiratory control: the role of the vagus nerve. Respir Physiol Neurobiol 2011; 178: 387-394.
Tracey KJ. Reflex control of immunity. Nat Rev Immunol 2009; 9: 418-428.
Tully PJ, et al. A review of the affects of worry and generalized anxiety disorder upon cardiovascular health and coronary heart disease. Psychol Health Med 2013; 18: 627-644.
Vanoli E, et al. Vagal stimulation and prevention of sudden death in conscious dogs with a healed myocardial infarction. Circ Res 1991; 68: 1471-1481.
Wang, Z. et al. Chronic intermittent low-level transcutaneous electrical stimulation of auricular branch of vagus nerve improves left ventricular remodeling in conscious dogs with healed myocardial infarction. Circ Heart Fail 7, 1014-1021 (2014).
Wang, Z. et al. Low-level transcutaneous electrical stimulation of the auricular branch of vagus nerve ameliorates left ventricular remodeling and dysfunction by downregulation of matrix metalloproteinase 9 and transforming growth factor ß1. J. Cardiovasc. Pharmacol. 65, 342-348 (2015).
Webster KM, et al. Progesterone treatment reduces neuroinflammation, oxidative stress and brain damage and improves long-term outcomes in a rat model of repeated mild traumatic brain injury. J Neuroinflammation 2015; 12: 238.
Wehrwein EA, et al. Regulation of blood pressure by the arterial baroreflex and autonomic nervous system. Handb Clin Neurol 2013; 117: 89-102.
Weiser MJ, et al. Estrogen receptor-beta agonist diarylpropionitrile: biological activities of Rand S-enantiomers on behavior and hormonal response to stress. Endocrinology 2009; 150: 1817-1825.
Wellens HJJ, et al. Risk stratification for sudden cardiac death: current status and challenges for the future. Eur Heart J 2014; 35: 1642-1651.
World Health Organization | Depression. 2016. http://www.who.int/mediacentre/factsheets/fs369/en/ (accessed Jan. 29, 2016).
Yu L, et al. Low-level transcutaneous electrical stimulation of the auricular branch of the vagus nerve: a noninvasive approach to treat the initial phase of atrial fibrillation. Heart Rhythm Off J Heart Rhythm Soc 2013; 10: 428-435.
Zamotrinsky A, et al. Effects of electrostimulation of the vagus afferent endings in patients with coronary artery disease. Coron Artery Dis 1997; 8: 551-557.
Zamotrinsky AV, et al. Vagal neurostimulation in patients with coronary artery disease. Auton Neurosci Basic Clin 2001; 88: 109-116.
Zannad, F. et al. Chronic vagal stimulation for the treatment of low ejection fraction heart failure: results of the NEural Cardiac TherApy foR Heart Failure (NECTAR-HF) randomized controlled trial. Eur. Heart J. 36, 425-433, doi:10.1093/eurheartj/ehu345 (2015).
Zhang Y, et al. Chronic vagus nerve stimulation improves autonomic control and attenuates systemic inflammation and heart failure progression in a canine high-rate pacing model. Circ Heart Fail 2009; 2: 692-699.
Zoccal DB, et al. The nucleus of the solitary tract and the coordination of respiratory and sympathetic activities. Front Physiol 2014; 5: 238.
Ahboucha S, et al. The neurosteroid system: an emerging therapeutic target for hepatic encephalopathy. Metab Brain Dis 2007; 22: 291-308.

(56) References Cited

OTHER PUBLICATIONS

Akiyama T, et al. Effects of right and left vagal stimulation on left ventricular acetylcholine levels in the cat. Acta Physiol Scand 2001; 172: 11-16.
Al-Din A, et al. Trigeminal cephalgias and facial pain syndromes associated with autonomic dysfunction. Cephalalgia 2005; 25: 605-611.
Almas, A. et al. Depression is linked to uncontrolled hypertension: a case-control study from Karachi, Pakistan. J Ment Health 23, 292-296, doi:10.3109/09638237.2014.924047 (2014).
Annoni EM, et al. Intermittent electrical stimulation of the right cervical vagus nerve in salt-sensitive hypertensive rats: effects on blood pressure, arrhythmias, and ventricular electrophysiology. Physiol Rep 2015; 3. doi:10.14814/phy2.12476.
Appelhans BM, et al. Heart rate variability and pain: associations of two interrelated homeostatic processes. Biol Psychol 2008; 77: 174-182.
Bedi US, et al. Cardiovascular manifestations of posttraumatic stress disorder. J Natl Med Assoc 2007; 99: 642-649.
Benarroch EE. The central autonomic network: functional organization, dysfunction, and perspective. Mayo Clin Proc 1993; 68: 988-1001.
Billman GE, et al. Baroreceptor reflex control of heart rate: a predictor of sudden cardiac death. Circulation 1982; 66: 874-880.
Blechert J, et al. Autonomic and respiratory characteristics of posttraumatic stress disorder and panic disorder. Psychosom Med 2007; 69: 935-943.
Bohning DE, et al. Feasibility of vagus nerve stimulation-synchronized blood oxygenation level-dependent functional MRI. Invest Radiol 2001; 36: 470-479.
Bonaz, B., et al. Vagal tone: effects on sensitivity, motility, and inflammation. Neurogastroenterol Motil 28, 455-462, doi:10.1111/nmo.12817 (2016).
Browning, K. N. et al. Plasticity of vagal brainstem circuits in the control of gastric function. Neurogastroenterol Motil 22, 1154-1163, doi:10.1111/j.1365-2982.2010.01592.x (2010).
Brudey C, et al. Autonomic and inflammatory consequences of posttraumatic stress disorder and the link to cardiovascular disease. Am J Physiol Regul Integr Comp Physiol 2015; 309: R315-321.
Brunton, P. J. et al. 5a-Reduced neurosteroids sex-dependently reverse central prenatal programming of neuroendocrine stress responses in rats. J. Neurosci. 35, 666-677, doi:10.1523/JNEUROSCI.5104-13.2015 (2015).
Brunton, P. J. et al. Endogenous opioids and attenuated hypothalamic-pituitary-adrenal axis responses to immune challenge in pregnant rats. J. Neurosci. 25, 5117-5126, doi:10.1523/JNEUROSCI.0866-05.2005 (2005).
Buckley TC, et al. A meta-analytic examination of basal cardiovascular activity in posttraumatic stress disorder. Psychosom Med 2001; 63: 585-594.
Chae, J.-H. et al. A review of functional neuroimaging studies of vagus nerve stimulation (VNS). J Psychiatr Res 37, 443-455 (2003).
Chalmers JA, et al. Anxiety Disorders are Associated with Reduced Heart Rate Variability: A Meta-Analysis. Front Psychiatry 2014; 5: 80.
Chiou, C. W., et al. Efferent vagal innervation of the canine atria and sinus and atrioventricular nodes. The third fat pad. Circulation 95, 2573-2584 (1997).
Clancy, J. A. et al. Non-invasive vagus nerve stimulation in healthy humans reduces sympathetic nerve activity. Brain Stimulation 7, 871-877, doi:10.1016/j.brs.2014.07.031 (2014).
Cohen, H. et al. Autonomic dysfunction in patients with fibromyalgia: application of power spectral analysis of heart rate variability. Semin. Arthritis Rheum. 29, 217-227 (2000).
Daban, C., et al. Safety and efficacy of Vagus Nerve Stimulation in treatment-resistant depression. A systematic review. J Affect Disord 110, 1-15, doi:10.1016/j.jad.2008.02.012 (2008).
Davies SJC, et al. Anxiety and cardiovascular disease. Mod Trends Pharmacopsychiatry 2013; 29: 85-97.
De Ferrari GM, et al. Chronic vagus nerve stimulation: a new and promising therapeutic approach for chronic heart failure. Eur Heart J 2011; 32: 847-855.
De Ferrari GM, et al. Pharmacologic modulation of the autonomic nervous system in the prevention of sudden cardiac death. A study with propranolol, methacholine and oxotremorine in conscious dogs with a healed myocardial infarction. J Am Coll Cardiol 1993; 22: 283-290.
De Ferrari GM, et al. Vagal reflexes and survival during acute myocardial ischemia in conscious dogs with healed myocardial infarction. Am J Physiol 1991; 261: H63-69.
De Vries HE, et al. Neuroinflammation: A common denominator for stroke, multiple sclerosis and Alzheimer's disease. Biochim Biophys Acta 2015. doi:10.1016/j.bbadis.2015.12.024.
Dergacheva, O., et al. Respiratory modulation of premotor cardiac vagal neurons in the brainstem. Respir Physiol Neurobiol 174, 102-110, doi:10.1016/j.resp.2010.05.005 (2010).
Di Michele F, et al. Neurosteroid and neurotransmitter alterations in Parkinson's disease. Front Neuroendocrinol 2013; 34: 132-142.
Dockray, G. J. Enteroendocrine cell signalling via the vagus nerve. Current opinion in pharmacology 13, 954-958, doi:10.1016/j.coph.2013.09.007 (2013).
Dockray, G. J. Gastrointestinal hormones and the dialogue between gut and brain. J Physiol 592, 2927-2941, doi:10.1113/jphysiol.2014.270850 (2014).
Dubé A-A, et al. Brain activity associated with the electrodermal reactivity to acute heat pain. NeuroImage 2009; 45: 169-180.
Ellrich, J. Transcutaneous Vagus Nerve Stimulation. Eur Neurol Rev 6, 254-256 (2011).
Englot, D. J., et al. Vagus nerve stimulation for epilepsy: a meta-analysis of efficacy and predictors of response. J. Neurosurg. 115, 1248-1255, doi:10.3171/2011.7.JNS11977 (2011).
Fallgaiter, A. J. et al. Far field potentials from the brain stem after transcutaneous vagus nerve stimulation. J Neural Transm (Vienna) 110, 1437-1443, doi:10.1007/s00702-003-0087-6 (2003).
Fang J, et al. Transcutaneous Vagus Nerve Stimulation Modulates Default Mode Network in Major Depressive Disorder. Biol Psychiatry 2016; 79: 266-273.
Farrell, T. G. et al. Prognostic value of baroreflex sensitivity testing after acute myocardial infarction. Br Heart J 67, 129-137 (1992).
Fisher H, et al. Acute effects of respiratory-gated auricular vagal afferent nerve stimulation (RAVANS) in the modulation of blood pressure in hypertensive patients. In: Computing in Cardiology conference, Maastricht, the Netherlands, 2018. Comput Cardiol vol. 45. IEEE, 2018.
Frangos, E., et al. Non-invasive Access to the Vagus Nerve Central Projections via Electrical Stimulation of the External Ear: fMRI Evidence in Humans. Brain Stimulation 8, 624-636, doi:10.1016/j.brs.2014.11.018 (2015).
Freedland KE, et al. Effect of depression on prognosis in heart failure. Heart Fail Clin 2011; 7: 11-21.
Gao XY, et al. Acupuncture-like stimulation at auricular point Heart evokes cardiovascular inhibition via activating the cardiac-related neurons in the nucleus tractus solitarius. Brain Res 2011; 1397: 19-27.
Garcia RG, et al. Respiratory-gated auricular vagal nerve stimulation lowers blood pressure in hypertensive patients. In: Scientific Sessions, American Heart Association, Anaheim, CA, 2017. Circulation. Nov. 12, 2017; 136: A21014.
García-Gómez RG, et al. [The role played by the autonomic nervous system in the relation between depression and cardiovascular disease]. Rev Neurol 2007; 44: 225-233. English Abstract.
Garland EL. Pain processing in the human nervous system: a selective review of nociceptive and biobehavioral pathways. Prim Care 2012; 39: 561-571.
George, M. S. et al. Vagus nerve stimulation: a new form of therapeutic brain stimulation. CNS Spectr 5, 43-52 (2000).
Gilbey, M. P., et al. Synaptic mechanisms involved in the inspiratory modulation of vagal cardio-inhibitory neurones in the cat. J. Physiol. (Lond.) 356, 65-78 (1984).
Gold, M. R. et al. Vagus Nerve Stimulation for the Treatment of Heart Failure: The INOVATE-HF Trial. J Am Coll Cardiol, doi:10.1016/j.jacc.2016.03.525 (2016).

(56) References Cited

OTHER PUBLICATIONS

Goldstein JM, et al. Disruption of fetal hormonal programming (prenatal stress) implicates shared risk for sex differences in depression and cardiovascular disease. Front Neuroendocrinol 2014; 35: 140-158.

Gonzalez C, et al. Carotid body chemoreceptors: from natural stimuli to sensory discharges. Physiol Rev 1994; 74: 829-898. In three parts due to file size.

* cited by examiner

SYSTEMS AND METHODS FOR RESPIRATORY-GATED NERVE STIMULATION

CROSS-REFERENCE TO RELATED APPLICATIONS

This application represents the national stage entry of PCT International Application No. PCT/US2018/041485 filed Jul. 10, 2018, which claims the benefit of U.S. Provisional Patent Application Ser. No. 62/530,913 filed on Jul. 11, 2017 and entitled "Respiratory-Gated Nerve Stimulation", incorporated herein by reference in their entirety.

STATEMENT REGARDING FEDERALLY SPONSORED RESEARCH

This invention was made with government support under OD023867, and MH103468 awarded by the National Institutes of Health. The government has certain rights in the invention.

BACKGROUND

The electrical stimulation of biological systems to affect the stability or performance of a physiological system can provide functional and/or therapeutic outcomes, and has been used for activating target muscles or nerves to provide relief for a variety of disorders. Such stimulation may be delivered to tissue and target a muscle or a nerve, often afferent nerves. Many systems use stimulators (i.e., pulse generators) and electrodes to deliver electrical charge to the target site of the muscle or nerve. For example, electrical stimulation of the vagus nerve (VNS) is a validated therapy approved by United States Food and Drug Administration that has improved the lives of many individuals with epilepsy or depression. For example, implantable VNS has been reported to have improved effects on seizure reduction in epileptic patients, and mood elevation effects in depression patients.

Implantable cervical vagus nerve stimulation (iVNS) is a neuromodulatory technique used for managing epilepsy and treatment-resistant major depressive disorder (MDD). Traditionally, iVNS requires the pectoral implantation of a neurostimulating device connected to an electrode placed around the cervical branch of the vagus nerve. Despite beneficial effects of iVNS, this technique is associated with significant side effects and surgical morbidity, limiting broad applicability. Recently, a new non-invasive neuromodulation method, which electrically stimulates the Auricular Branch of the Vagus Nerve (ABVN), called auricular transcutaneous vagus nerve stimulation (a-tVNS) has been proposed. The ABVN is the only peripheral branch of the vagus that distributes to the skin, innervating the auricle at specific sites. Central projections of ABVN signaling, using transganglionic horseradish peroxidase (HRP) transport in animal studies, have identified interstitial, dorsal, dorsolateral and commissural subnuclei of ipsilateral nucleus tractus solitarii (NTS). In humans, brainstem far-field evoked potentials have been noted for ABVN stimulation, and fMRI studies have demonstrated blood oxygen level dependent (BOLD) signal increase in brainstem areas such as NTS and bilateral spinal trigeminal nucleus, corroborating results obtained with classical iVNS. Some studies have also shown that ABVN stimulation activates cortical networks implicated in autonomic control as well as affect regulation such as amygdala, hippocampus, anterior cingulate and insula, with the potential for positive effects on mood symptomatology of individuals with major depression. Additional evidence has also suggested that ABVN stimulation can regulate cardiac electrophysiology resulting in inhibition of atrial fibrillation and reversal of left ventricular remodeling. In humans, ABVN stimulation has been observed to reduce blood pressure and exert an antiarrhythmic effect. Initial clinical studies with a-tVNS have also shown positive effects in reduction of peripheral sympathetic nerve activity with concomitant increase in parasympathetic nerve activity, improvement of left ventricular function and suppression of atrial fibrillation.

Recent evidence suggests that VNS may have anti-nociceptive effects, particularly in patients with depression. Animal studies have linked stimulation of vagal afferents with antinociception. Both animal studies and recent human studies suggest that during active VNS, pro-nociception can occur when stimulus intensity is low (e.g., about 30-60% of pain threshold, or approximately 0.5-2 mA or more or less), but anti-nociceptive effects predominate when stimulus intensity is high (e.g., just below or above pain threshold, or approximately greater than 2.5 mA or more or less). Moreover, chronic VNS may raise pain thresholds (i.e., analgesia) for both tonic pinch and heat pain, as well mitigating the so-called pain wind-up phenomenon (a phenomenon related to central sensitization) when mechanical stimuli are applied. These results have been promising in terms of analgesia. Moreover, VNS has the advantage of greater side effects tolerance since nerve stimulation is targeted therapy, as compared to pharmacotherapy is systemic.

Unfortunately, classical i-VNS can also induce morbidity stemming either from co-activation of efferent vagal fibers (e.g., bradycardia, asystole, larynx/pharynx disorders, dysphagia), or from infection or hardware failure due to the invasive nature of i-VNS systems. I-VNS systems typically require open surgery to implant one or more electrodes on or near the vagus nerve, and may also include tunneling a lead to connect the electrodes to a pulse generator also implanted under the skin. The application of a less invasive vagus nerve stimulation therapy would allow VNS benefits to reach a larger percentage of afflicted populations.

Spinal cord stimulation (SC S) is an established therapy in the treatment of back and limb pain, as well as angina. Despite many years of use, and many successes, there is an opportunity to improve SCS therapy. Not all patients respond to the therapy and in a substantial number the response is less than clinically desired.

Therefore, it would be an advance in the art to provide improved systems and methods for delivering electrical stimulation.

SUMMARY OF THE DISCLOSURE

The present disclosure overcomes the aforementioned drawbacks by providing systems and methods for neurostimulation to provide therapeutic outcomes, such as the treatment of hypertension, inflammatory disorders, cardiovascular disease, chronic pain, mood and anxiety disorders, disorders associated with chronic hypoxia/hypercapnia, primary autonomic system disorders and gastrointestinal disorders with signals that are adjusted based on pulmonary or respiratory activity. The neurostimulation may target to the spinal cord, the vagus nerve and/or its branches, or the like. In particular, the systems and methods of the present disclosure can use a detecting device to detect pulmonary activity. Specific time points in the respiratory signal are identified where central autonomic nuclei may be more receptive to afferent input. When these specific points are identified, such as during an exhalation phase of the respiratory cycle, a stimulator can be controlled to provide neurostimulation to at least one auricular branch of a vagus nerve, or to a cervical branch of the vagus nerve, or to a spinal cord of the subject. In this regard, the neurostimulation timing is advantageously correlated to the detected respiratory activity providing improved therapeutic outcomes.

In one configuration, an apparatus is provided that includes an electrode configured to be electrically coupled to an afferent nerve fiber of a vagus nerve of a subject and a stimulation circuit connected to the electrode to deliver a stimulation signal to the electrode, thereby stimulating the afferent nerve fiber. The apparatus also includes at least one processor configured to determine a pulmonary characteristic of the subject and deliver the stimulation signal to the stimulation circuit to effectuate electrical stimulation of the subject based on the pulmonary characteristic of the subject.

In one configuration, an apparatus is provided that includes an electrode adapted to be electrically coupled to an afferent nerve fiber in a cervical branch of a vagus nerve of a subject and a stimulation circuit connected to the electrode to deliver a signal to the electrode to stimulate the afferent nerve fiber. The apparatus also includes a detection device adapted to detect pulmonary activity of the subject and convert the detected pulmonary activity into a corresponding detection signal and a controller in communication with each of the stimulation circuit and the detection device to receive the detection signal and control the stimulation signal based on the detection signal.

In one configuration, an apparatus is provided that includes an electrode adapted to be electrically coupled to nerves in or near a spinal cord (including the dorsal roots and the spinal cord itself—collectively the "spinal cord" nerves) of a subject and a stimulation circuit connected to the electrode to deliver a signal stimulation to stimulate the spinal cord nerves. The apparatus also includes a detection device adapted to detect pulmonary activity of the subject and convert the detected pulmonary activity into a corresponding detection signal. The apparatus further includes a controller in communication with each of the stimulation circuit and the detection device to receive the detection signal, determine a trigger, and, based on the trigger, cause the stimulation circuit to deliver the stimulation signal to the subject.

In one configuration, a method is disclosed for providing a neurostimulation to a subject. The method includes receiving a signal from a detection device detecting pulmonary activity of a patient. Time points are identified in the signal where central autonomic nuclei are receptive to afferent input. A stimulation signal is sent to an electrode that is electrically coupled to a subject when the time points are identified.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
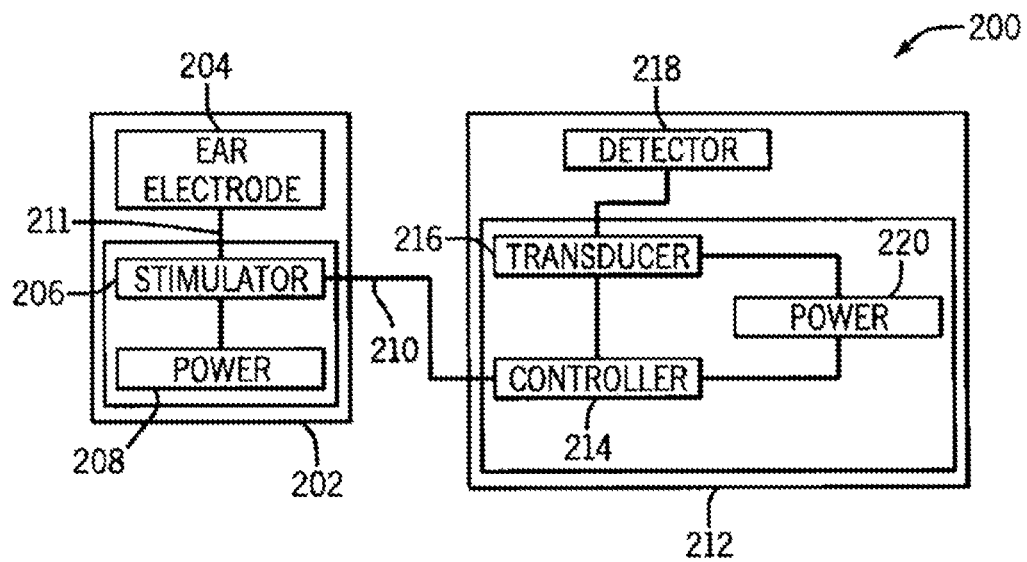
FIG. 1 is a schematic diagram of an example respiratory-gated vagal afferent nerve stimulation apparatus.

In one configuration of the present disclosure, systems and methods for delivering neurostimulation are provided. The neurostimulation may be delivered to an auricular branch of the vagus nerve. The system may include components of and/or may operate as respiratory-gated auricular vagal afferent nerve stimulation (RAVANS). Neurostimulation may be provided to afferent fibers of the auricular branch of the vagus nerve (ABVN). Such neurostimulation may be performed to treat hypertension, inflammatory disorders, or gastrointestinal disorders. The neurostimulation can be simultaneously synchronized to the pulmonary activity of an individual. In one configuration, the stimulation can be gated to specific phases of the respiratory cycle. For example, the ABVN may be stimulated during a specific phase of respiration, such as inspiration or expiration. In another configuration, a stimulation paradigm may be gated to levels of carbon dioxide concentration, as measured non-invasively in blood or expired air, with preselected triggers set within the respiratory cycle.

In one configuration of the present disclosure, systems and methods for neurostimulation are provided to stimulate fibers of the cervical section of the vagus nerve. Such neurostimulation may be deployed to treat conditions such as epilepsy, hypertension, depression, cardiovascular disease, inflammation-associated disorders, chronic pain, anxiety disorders, disorders associated with chronic hypoxia/hypercapnia, primary autonomic system disorders and the like. The neurostimulation can be simultaneously synchronized to the pulmonary activity of the patient. In one configuration, the stimulation can be gated to specific phases of the respiratory cycle. For example, the vagus nerve may be stimulated during a specific phase of respiration, such as inspiration or expiration. In another configuration, a stimulation paradigm may be gated to levels of carbon dioxide concentration, as measured non-invasively in blood or expired air.

In one configuration of the present disclosure, systems and methods are provided for neurostimulation of the spinal cord that may be synchronized to the pulmonary activity of the patient. Such neurostimulation may be performed to treat cardiovascular disease, chronic pain, and the like. In one configuration, the stimulation may be gated to specific phases of the respiratory cycle. For example, the neurostimulation may be stimulated during a specific phase of respiration, such as inspiration or expiration.

A respiration-gated neuromodulation system in accordance with the present disclosure may be used to deliver electrical stimulation to at least one afferent nerve fiber in an auricular branch of a vagus nerve of a patient. As will be described, the stimulation may be controlled or varied based on the pulmonary activity of the patient. In one implementation, an electrode (e.g., percutaneous, implanted, or surface) is placed in electrical conductive contact (i.e., electrically coupled; the electrode proximity to the excitable nerve fibers allows current flow from the electrode to excite the nerve) with the auricular branch of the vagus nerve. Pulmonary activity is monitored, such as in real-time, to determine functional components of the pulmonary activity, such as timing. The functional components can be compared to preselected characteristics in the pulmonary activity to control, adjust, or trigger selective neurostimulation of the auricular branch of the vagus nerve based thereon.

A respiratory-gated neuromodulation system in accordance with the present disclosure can facilitate minimally or non-invasive isolation of afferent fibers in vagus nerve stimulation thereby reducing deleterious effects due to vagal efferent stimulation. Moreover, a non-invasive system in accordance with the present disclosure can reduce infection-associated morbidity typically due to surgical intervention, when compared to traditional stimulation systems, such as described above in the Background.

A system in accordance with the present disclosure can provide minimally invasive or non-invasive therapy for various medical conditions, such as epilepsy, depression, overeating, Alzheimer's disease, chronic pain, or combinations thereof, and the like. Other uses of respiration-gated neuromodulation can include control against fatal arrhythmias, hypertension, improving autonomic balance, restoring parasympathetic/sympathetic tone in hypertrophic cardiac myopathy, increasing coronary blood flow, decreasing anginal symptoms, reducing anxiety and mood disorders, and providing treatments for migraines and fibromyalgia, as non-limiting examples. In some implementations, a respiration-gated neuromodulation system in accordance with the present disclosure can be utilized to treat chronic pelvic pain (CPP) patients with both low and high psychiatric co-morbidity, a subpopulation which has been notoriously difficult to treat and is in need of new, innovative therapies Referring to FIG. 1, a schematic diagram of an example respiratory-gated auricular vagal afferent nerve stimulation (RAVANS) based apparatus 200 in accordance with the present disclosure is illustrated. The example RAVANS-based apparatus 200 can include an ear-based device 202, a pulmonary-based device 212, and a link 210 between the ear-based device 202 and the pulmonary-based device 212. The link 210 can be either wireless (e.g., radio-frequency, RF, Bluetooth, or the like) or a wired cable-link. It is to be appreciated that the RAVANS-based apparatus 200 may have other configurations.

In one configuration, the ear-based device 202 includes at least one ear electrode 204, a stimulator 206 connected to the ear electrode 204, and a power module 208 connected to the stimulator 206. The ear electrode 204 of the ear-based device 202 may be a percutaneous electrode that penetrates the skin, or a surface electrode that is placed on the skin. In one configuration, the percutaneous electrode may be about 0.1-0.3 mm in diameter and about 2-5 mm in length. The percutaneous electrode 204 may be manufactured from stainless steel, titanium, platinum or other conductive material suitable for insertion in the skin and may have a very fine tip. Alternatively, or in combination, one or more surface electrodes may be used. The surface electrodes may include a small disc (e.g., about 2-5 mm diameter) made from a conductive material (e.g., stainless steel, gold, conductive rubber) and attached to the patient, for example, using an adhesive band. Similarly, pre-gelled circular or spherical silver/silver chloride electrodes (about 5-10 mm diameter) can be used. It is to be appreciated that a variety of electrode configurations known to one of skill in the art may be used with the RAVANS-based apparatus 200.

Figures 2A, 2B:
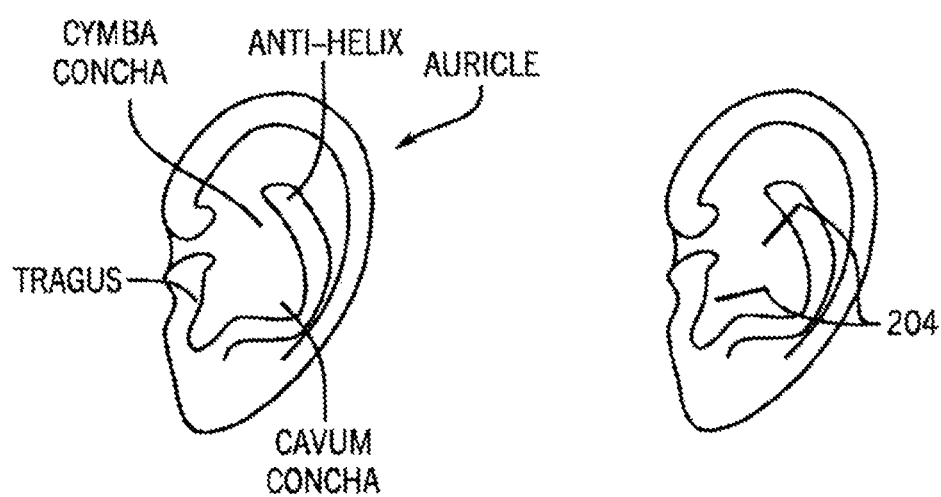
FIG. 2A is an anatomical view of an auricle.
FIG. 2B is an anatomical view of FIG. 2A showing an exemplary placement of electrodes to electrically connect to an auricular branch of an afferent vagus nerve.

Referring to FIGS. 1, 2A, and 2B, a first ear electrode 204 (e.g., anode), which may be a percutaneous, implanted, or surface electrode, is placed in electrical conductive contact with afferent receptors of the ABVN, such as located in the cymba concha of the ear of an individual. The stimulator 206 can be connected to each of the ear electrodes 204 to stimulate the corresponding afferent nerve fibers. A detection device 218 can be included that is adapted to detect pulmonary activity of the individual and determine functional characteristics from the pulmonary activity that can then be used to operate or coordinate stimulation. As one non-limiting example, the detected pulmonary activity can be converted to an activity signal that is used to detect activity indicative of functional characteristics to trigger delivery of neurostimulation. For example, the detection device 218 can communicate a trigger to the controller 214 to trigger the stimulator 206 to generate an output signal or may provide an output signal for the stimulator 206 to deliver. The detection device 218 and the controller 214 may be formed by separate components and systems, or may simply reflect functions performed, for example, by a common system, processor, or controller. Similarly, the controller 214 and stimulator 206 may be discrete or distinct components or systems, or may share components and/or be controlled and operated by a common system, processor, or controller. Regardless of the particular hardware and software architecture, the stimulator 206 is configured to generate a neurostimulation signal to the ear electrodes 204.

It is to be appreciated that the electrode 204 may include a multi-contact electrode, such as a bipolar electrode. It is also to be appreciated that the electrode need not be specifically placed in or on or near the cymba concha. Both the cymba concha and cavum concha regions have been shown to be innervated by the auricular branch of the afferent vagus nerve. The ear electrode 204 can be connected to the stimulator 206 by a link 211, which may include insulated and shielded (e.g., radio frequency shielded) conductive leads. Alternatively, or in combination, the link 211 may be a wireless connection, such as through radio frequency transponders and receivers.

In some configurations, the stimulator 206 and/or other components including the controller 214, may be housed in an enclosure sized and configured to be placed behind or over the auricle. The auricle itself can be used to physically support the stimulator 206 and power supply for the ear-based device 202. Alternatively, the stimulator 206 may take input from a remotely-located controller 214 (e.g., a microchip and/or computer), such as may be located on the pulmonary-based device 212. The stimulator 206 may output its signal to an ear electrode (e.g., either anode or cathode) 204 via insulated and shielded conductive leads, as described above, and receive the return signal via a return electrode.

The stimulator 206 may deliver various electrical signals to the vagus nerve using ear electrode 204. In one non-limiting example, the stimulator 206 may deliver a constant-current burst of bi-phasic square wave pulses. These pulses or other pulse architectures may be delivered at a frequency of about 1-100 Hz (or higher frequencies including up to about 20 KHz in some applications). These stimulations or others may be delivered with a non-limiting current intensity in a range of 0.25 mA to 20 mA. Each pulse may have a pulse width that, in some non-limiting examples, may vary from about 100-1000 microseconds. The burst timing of the burst can depend on an algorithm used to trigger the stimulation or the particular functional characteristics of the pulmonary signal and whether the burst is a fixed duration, is a percentage of the measured respiratory rate, terminates at a detected phase of the respiratory cycle, or is based on some other algorithms implemented by the RAVANS-based apparatus 200. For example, the burst may begin upon detection of the expiration phase of the respiratory signal. In one non-limiting example, the burst may continue for 25% of the average measured respiratory interval.

The power module 208 may provide power, such as from an energy storage device or battery, to the stimulator 206. In one non-limiting example, the power module may be configured to supply 1.5-9 volts. The power module 208 may be housed, but need not be housed, inside the same enclosure as the stimulator 206 and can be connected to the stimulator 206 with insulated leads. For example, the power module 208 may include a battery that can be rechargeable, e.g., a recharger may recharge the battery while it remains in the device 202, or the battery may be removed for recharging, depending on specifications and/or applications. Additionally or alternatively, the power module 208 may also include or comprise a non-rechargeable battery.

As described, in one non-limiting configuration, the pulmonary-based device 212 may include the controller 214. Whether or not the controller 214 is integrated with the pulmonary-based device 212, a transducer 216, a detector 218, such as a pulmonary activity detector (e.g., a respiratory belt with a strain gage or a nasal air flow detector), and a power supply 220, may be integrated with the pulmonary-based device.

Figure 3:
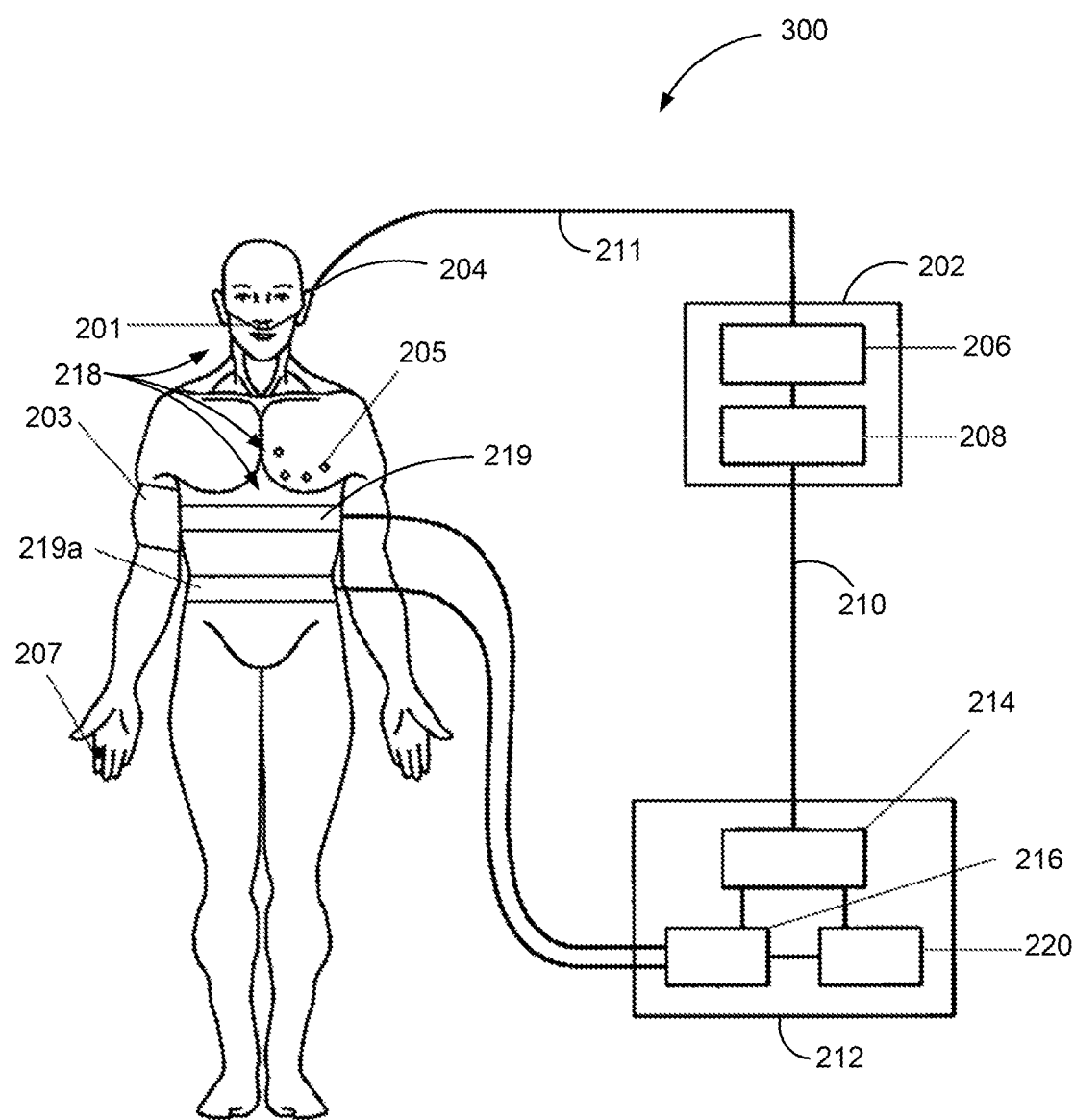
FIG. 3 is a schematic diagram of an example respiratory-gated auricular vagal afferent nerve stimulation (RAVANS) deployed to provide an example neurostimulation regiment to a patient.

In one non-limiting configuration illustrated in FIG. 3, the detector 218 may be a respiratory belt 219, a nasal cannula 201, chest electrodes 205, or other detection system. The respiratory belt 219 may be placed around the rib-cage portion of the thorax of a patient. The respiratory belt may be non-elastic and can be made from woven fabric or another material. To illustrate, the respiratory belt may be equipped with a serial pneumatic bellow(s) (where pressure inside the bellows may vary based on lung volume), a strain gage, or a piezoelectric device that is also in serial with the belt fabric, or a combination thereof. The bellows can be made from SILASTIC rubber or similar material. If the bellows are used, a low-compliance TYGON tubing may connect the airspace inside the bellows with the pressure transducer. If the strain gage or the piezoelectric device is used, its output can be connected to the transducer 216 with insulated and shielded conductive leads known in the art.

Figure 4:
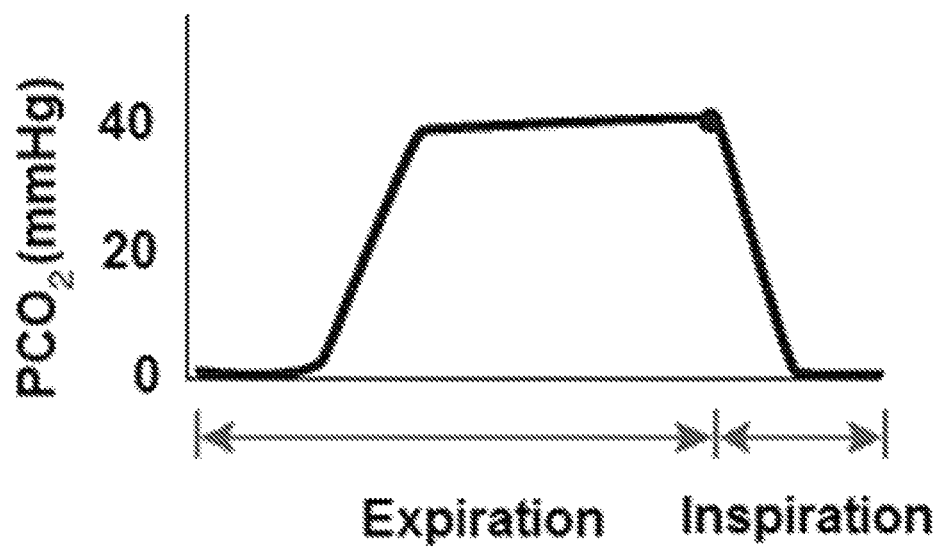
FIG. 4 is a graph of PCO2 levels with pulmonary activity showing respiratory cycles of inspiration and expiration.

The nasal cannula 201 may be configured to extend to receive airflow expelled from the nose of the patient. Thus, as illustrated, the nasal cannula 201 may extend about the face and under the nose to receive expelled air. Referring to FIG. 4, a waveform signal describing the changes in carbon dioxide concentrations during the respiratory cycle may be collected. In another implementation, carbon dioxide detection can utilize an optical transcutaneous sampling cell for detection.

Regardless of the detection mechanism that is utilized, the transducer 216 may be an electrical, electro-mechanical, photovoltaic or other device that converts one type of energy to another. For example, the transducer 216 may convert either strain (from a strain gage), or air pressure (from bellows or from a nasal air flow detector) into a voltage signal. In one implementation, it may be included with and rest inside an enclosure on the respiratory belt 219, which may also contain the controller 214 or the power supply 220.

The controller 214 may be a device, which may include a computer-readable medium including code that, when executed by a processor, performs logical steps. The controller 214 may include circuitry capable of analyzing waveforms. The controller 214 may be configured to generate a trigger for the stimulator 206, or may be configured to operate to perform both the functions of the controller 214 described herein as well as controlling operation of the stimulator 206. In this way, the distinctiveness of the controller 214 and the stimulator 206 is virtual, such that two physical systems for the controller 214 and the stimulator are not present.

The power supply 220 may provide battery power to the transducer 216 and/or the controller 214. The power supply 220 may be housed inside the same enclosure as the transducer 216 and/or the controller 214 and may be connected with insulated leads known in the art. The battery may be rechargeable, e.g., a recharger may recharge the battery while it remains in the device 212, or the battery may be removed for recharging, depending on specifications and/or applications. The power supply 220 may also include or comprise a non-rechargeable battery.

As stated previously, it is to be appreciated that the RAVANS-based system 200 may have other configurations. For example, the power module 208 and the power supply 220 may be in the same device, or may be the same device. Alternatively, or in combination, the stimulator 206 may be housed outside of the ear-based device 202 such as inside the pulmonary-based device 212, for example. The ear-based device 202 may also include or be coupled to the detection device 218, such as when the detection device 218 is or includes nasal airflow detector that may be mechanically linked to a head piece that also houses a portion of the ear electrodes 204.

Referring to FIG. 3 in view of FIG. 2, an example of the RAVANS-based apparatus 200 of FIG. 2 can be used to provide a regimen of neurostimulation to a patient via a deployable patient system 300. As a non-limiting example, the system 300 of FIG. 3 may be specifically configured for treating hypertension, inflammatory disorders, gastrointestinal disorders, and the like. The patient may lay supine or may recline comfortably in a chair during the therapeutic RAVANS stimulation session.

As described above, the detector 218 may include a respiratory belt 219 to detect respiratory movements about the thorax. Other configurations are also possible. For example, the detector 218 may be a first respiratory belt 219 worn around the upper chest area and/or a second respiratory belt 219a worn around the abdominal area. If both the first and second respiratory belts 219, 219a are utilized, an algorithm may combine signals received from each of the respiratory belts, such as via the controller 214, to determine an overall respiratory activity of the patient. In another configuration, the detector 218 includes chest electrodes 205, which may be located on the chest of a patient. The detector 218 itself or the controller 214 may be adapted to evaluate changes in electrical impedance across the thoracic region over the respiratory cycle to detect respiratory movement.

The system may include pulse sensors 207 on the extremities to measure blood pressure in peripheral arteries and derive waveforms to calculate cardiac performance. A blood pressure cuff 203 or sphygmomanometer may also be used to measure blood pressure.

In one configuration, the stimulator 206 is configured with stimulus parameters that may vary depending on patient tolerance. In one non-limiting example, stimulation may be performed using a constant-current burst of bi-phasic square wave pulses at a frequency of about 1-100 Hz, or 20-50 Hz. In some non-limiting configurations or applications, higher frequencies including up to 20 kHz and/or current intensity in a range of 0.25 mA to 20 mA, or 1-3 mA may be desired. The pulse width may vary or be selected. In one non-limiting example, the pulse width may vary from about 100-1000 microseconds. The burst timing of the burst may depend on the algorithm used to trigger the stimulation based on the pulmonary activity. The burst may be a fixed duration, a percentage of the measured respiratory rate, terminate at a detected phase of the respiratory cycle, or be based on other algorithm parameters implemented in the controller 214. For one non-limiting example, the burst may begin upon detection of the expiration phase of the respiratory signal and continue for 25% of the average measured respiratory interval.

Two needles (e.g., sterile, disposable stainless steel silicon-coated filiform needles that are each about 0.16 mm wide and about 1.5 mm long) may be used as the anode and cathode electrodes 204, and may be inserted (or surface mounted) at sensitive (to palpation) points near the ABV, such as on, in, or near the cymba and/or cavum concha of the auricle of a single ear, as shown in FIG. 2B. In another implementation, another pair of needles may be inserted at the cymba and cavum concha of the other ear of the patient for bilateral stimulation of the left and right branches of the ABV. Acupuncture needles may be used to achieve electrical contact and to apply focal stimulation at the appropriate vagus nerve innervated sites. Corresponding leads 211 may be electrically attached to each of the perspective needles, or the needles may be incorporated into the electrode configuration, as shown.

In one non-limiting implementation, the stimulator 206 may be a constant-current stimulator that delivers bipolar pulses (pulse width of about 200 us), for example at about 15 Hz for about 1.5 seconds. Current intensity may be set to achieve moderate to strong (not painful) sensation. The respiratory belt 219 may be pneumatic and placed around the patient's lower thorax to access a respiratory cycle of the patient. For example, the respiratory belt 219 may be attached around the patient's chest and/or abdominal area. The respiratory belt 219 may have low-compliance tubing leading to a pressure transducer (e.g., PX138-0.3D5V, Omegadyne, Inc., Sunbury, Ohio), thereby producing voltage data that correspond to changes in respiratory volume. The voltage signal from the transducer 216 may be acquired, as a non-limiting example, at 200-500 Hz by the controller 214, such as a laptop-controlled device (e.g., National Instruments USB DAQCard 6009, 14 bit I/O, with LABVIEW® 7.1 data acquisition software).

The present disclosure provides a system that can utilize respiration information to control or implement neurostimulation. That is, respiration signals may be used to control tVNS effects on autonomic, immune and/or hormonal regulation. The present disclosure recognizes that, during each respiratory cycle, the heart rate slows during expiration and increases during inspiration, matching pulmonary blood flow to lung inflation and maintaining an appropriate oxygen diffusion gradient. This "respiratory sinus arrhythmia" (RSA) occurs by modulation of premotor cardiovagal neurons (e.g. nucleus ambiguus, NAmb) by diverse mechanisms, including afference (via NTS) from the lungs, as well as direct input from medullary respiratory neurons. Activation of excitatory 2nd-order neurons of the NTS during expiration increase premotor cardiovagal neuron firing rate and inhibit premotor sympathetic neurons. In contrast, during inspiration, activation of ventral respiratory group medullary neurons leads to increased inhibitory GABAergic synaptic transmission to premotor cardiovagal neurons. The regulatory role of respiration on NTS and premotor cardiovagal neurons is also affected by changes in cardiac output. During expiration there is an increase in cardiac output which induces a sudden elevation in mean arterial pressure and activation of baroreceptors located in the walls of the carotid artery sinus and aortic arch. This afferent neural feedback is relayed to NTS, which subsequently activates, via glutamatergic pathway, NMDA and non-NMDA receptors on the NAmb, and results in increased efferent parasympathetic signaling. As the dorsal medullary vagal system operates in response to variations in respiratory volumes, neuromodulation of the ABVN during specific phases of the respiratory cycle where NTS may be more receptive to afferent input (i.e. during expiration) could optimize the effects of tVNS on efferent sympathetic and parasympathetic autonomic modulation, immune and hormonal regulation, and the regulation of parasympathetic outflow.

Figure 5:
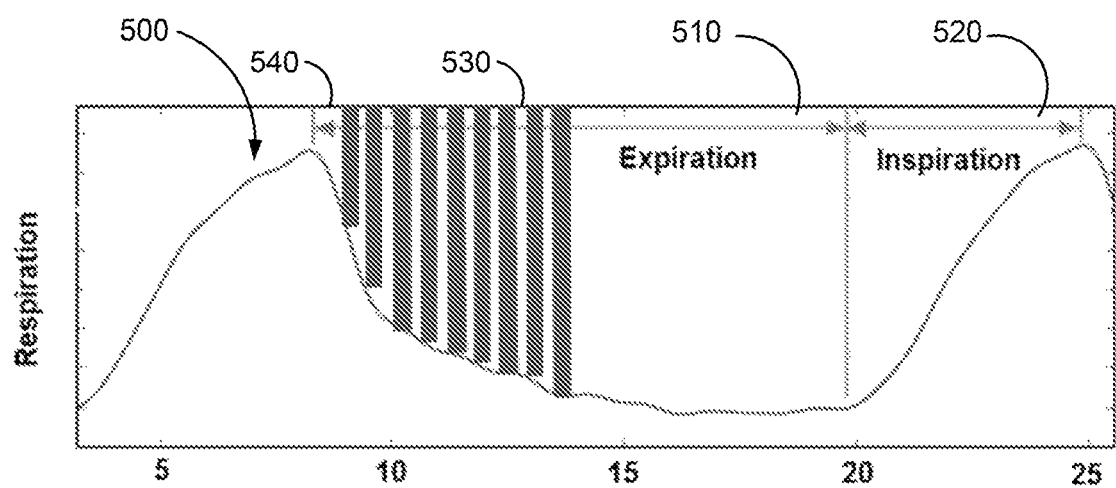
FIG. 5 is a graph of respiratory activity showing respiratory cycles of inspiration and expiration with example electrical signal patterns produced by the respiration-gated neuromodulation apparatus overlaid thereon.

Referring to FIG. 5 in view of FIG. 3, the controller 214 may detect different functional characteristics or functional features of the respiratory cycle 500 of the patient. For example, the controller 214 may detect end-inspiration 520 and end-expiration 510. This detection by the controller 214 may be performed in real-time or near-real-time. Once these temporal landmarks are determined, the controller 214 can produce an output, such as a TTL signal, that acts as a trigger to a high-frequency relay. Examples of such relays in the market place include: G6Z-1P-DC5 or G6J-2P-Y from Omron Electronics Components, Schaumburg, Ill. After the temporal landmark, the high-frequency relay may allow the stimulator 206 to pass current to the ear electrode 204 during either inspiration, expiration, intermittently, or combinations thereof in a regiment of neurostimulation to the patient with stimulations 530. That is, as illustrated, the stimulations 530 may be triggered to occur at a beginning of expiration 540 and extend through a portion of the expiration period to terminate prior to inspiration 520.

For example, the controller 214 may acquire the voltage signal from the transducer 216, for example, using a sampling rate of 20 Hz, and analyze this signal in real-time or near-real-time to find when inspiration and/or expiration has begun. The code or algorithm may use a low-pass filtered (as a non-limiting example, a cutoff frequency of about 10 Hz may be used) version of the respiratory signal. The average signal may be calculated, as a non-limiting example, every about 50 ms. This value may then be compared to a reference threshold. The reference threshold may be static or can be defined with an adaptive algorithm based on previous breaths. As one non-limiting example the previous five breaths may be used. A separate threshold may be defined for expiration and inspiration. If the current value is greater than the "high" threshold and if the previous landmark was for start-inspiration, then the current value becomes the start-expiration point. This process may continue until the current value is lower than the updating start-expiration point. The same process may be used to find the start-inspiration point, using the "low" threshold instead. The controller 214 may then send a trigger signal to the stimulator 206 (e.g., the ear-based device 202) at a pre-defined lag (one non-limiting example is about 0.5-1.0 seconds) from when inspiration and/or expiration has begun. The trigger signal may be a TTL pulse.

The above-described systems and methods may be used and/or adapted to treat or provide therapy for a variety of clinical conditions. The following provide a non-limiting description of how to utilize the above-described systems and methods for some non-limiting examples of clinical settings or treatments or therapies.

Use of the Above-Described RAVANS-Based System for the Treatment of Hypertension Blood pressure regulation involves a precise balance of excitatory and inhibitory transmitter systems in the brainstem. In response to blood pressure elevation, arterial baroreceptor discharge activates 2nd-order neurons of the NTS, leading to glutamatergic excitation of premotor cardiovagal neurons in NAmb. This results in increased efferent parasympathetic signaling to the sino-atrial and atrio-ventricular nodes. In addition, NTS neurons activate the caudal ventrolateral medulla (CVLM), which subsequently sends inhibitory fibers (GABAergic) to the rostral ventrolateral medulla (RVLM), decreasing premotor sympathetic neurons discharge, leading to blood pressure reduction. Previous studies have shown that angiotensin II (Ang II) exerts a tonic suppression, via GABAergic transmission in the NTS, of brainstem interactions involved in the modulation of autonomic function and baroreflex sensitivity. It has been suggested that the alteration of this brainstem autonomic circuitry could be involved in the pathogenesis of hypertension. The use of respiratory-gated modulation of the ABVN can have enhanced effects on the modulation of NTS and subsequent activation of NAmb and inhibition of RVLM, resulting in improvement of baroreflex sensitivity and blood pressure reduction in patients with hypertension. Thus, the above-described systems and methods can be deployed to this end.

Use of the Above-Described RAVANS-Based System for the Treatment of Inflammatory Disorders The modulation of brainstem autonomic nuclei and subsequently the activity of the cholinergic anti-inflammatory pathway by using RAVANS may have implications for the treatment of inflammation-associated disorders such as sepsis, rheumatoid arthritis, systemic lupus erythematosus, ulcerative colitis, Crohn's disease, diabetes mellitus, major depression, chronic obstructive pulmonary disease and asthma as non-limiting examples.

Vagus nerve stimulation has also shown promising effects in the regulation of metabolic alterations associated with obesity and cardiovascular risk such as insulin resistance and hyperglycemia. One mechanism explaining these beneficial effects could be the activation of the cholinergic anti-inflammatory pathway. Dysregulation of immune function in obesity is associated with low-degree chronic inflammation, a key intermediate step in the pathogenesis of insulin resistance and type 2 diabetes mellitus. Therefore, immune regulation elicited by RAVANS can result in enhancement of insulin sensitivity and reduction of metabolic complications in diabetic subjects. In fact, recent experimental studies have found an up-regulating effect in insulin receptor expression in the brain, liver and skeletal muscle after chronic vagal stimulation.

Besides its effects on systemic immune regulation, ABVN stimulation can also modulate neuroinflammation and neuroendocrine responses. Experimental studies have reported that NTS plays a critical role on the mediation of neurosteroids effects on the modulation of the Hypothalamic-Pituitary-Adrenal (HPA) and HPG (HP-gonadal) axes activity and neuroinflammation. Upregulation of neurosteroids production in the NTS has been associated with attenuated Adrenocorticotropic Hormone (ACTH) and corticosterone release in stressed rats. In addition, NTS is an area with high concentration of estrogen receptors-$\beta$ (ER-$\beta$) and previous studies have shown that the administration of ER-$\beta$ agonists is associated with decreased synthesis of noradrenergic enzymes in the NTS and reduced HPA response to stress. Because of the important role of NTS on neuroendocrine regulation, the modulation of its activity by using the above-described RAVANS-based system can be used for the treatment of disorders associated with impaired neurosteroid synthesis and increased neuroinflammation such as Parkinson's disease, multiple sclerosis, cerebrovascular disease, menopause, hepatic encephalopathy, and traumatic brain injury, and mood and anxiety disorders, among others.

Use of the Above-Described RAVANS-Based System for the Treatment of Gastrointestinal Disorders The vagus nerve plays an essential role in the physiology of the gastrointestinal tract via afferent mechanical and chemosensory signal transduction mechanisms. Impaired vagal regulation of gastrointestinal sensorimotor function has been suggested as one of the main pathophysiological alterations in diverse gastrointestinal pathologies. For instance, functional gastrointestinal disorders have been associated with a paucity of vagal tone leading to disturbed motility of the digestive tract, ineffectual emptying, fullness, bloating and visceral hyperalgesia. Thus, the enhanced modulation of parasympathetic outflow by the above-described RAVANS-based system may be used as part of a treatment strategy to alleviate symptomatology in disorders such as gastroparesis, functional dyspepsia, globus pharynges, functional dysphagia, irritable bowel syndrome and functional constipation.

Figure 6:
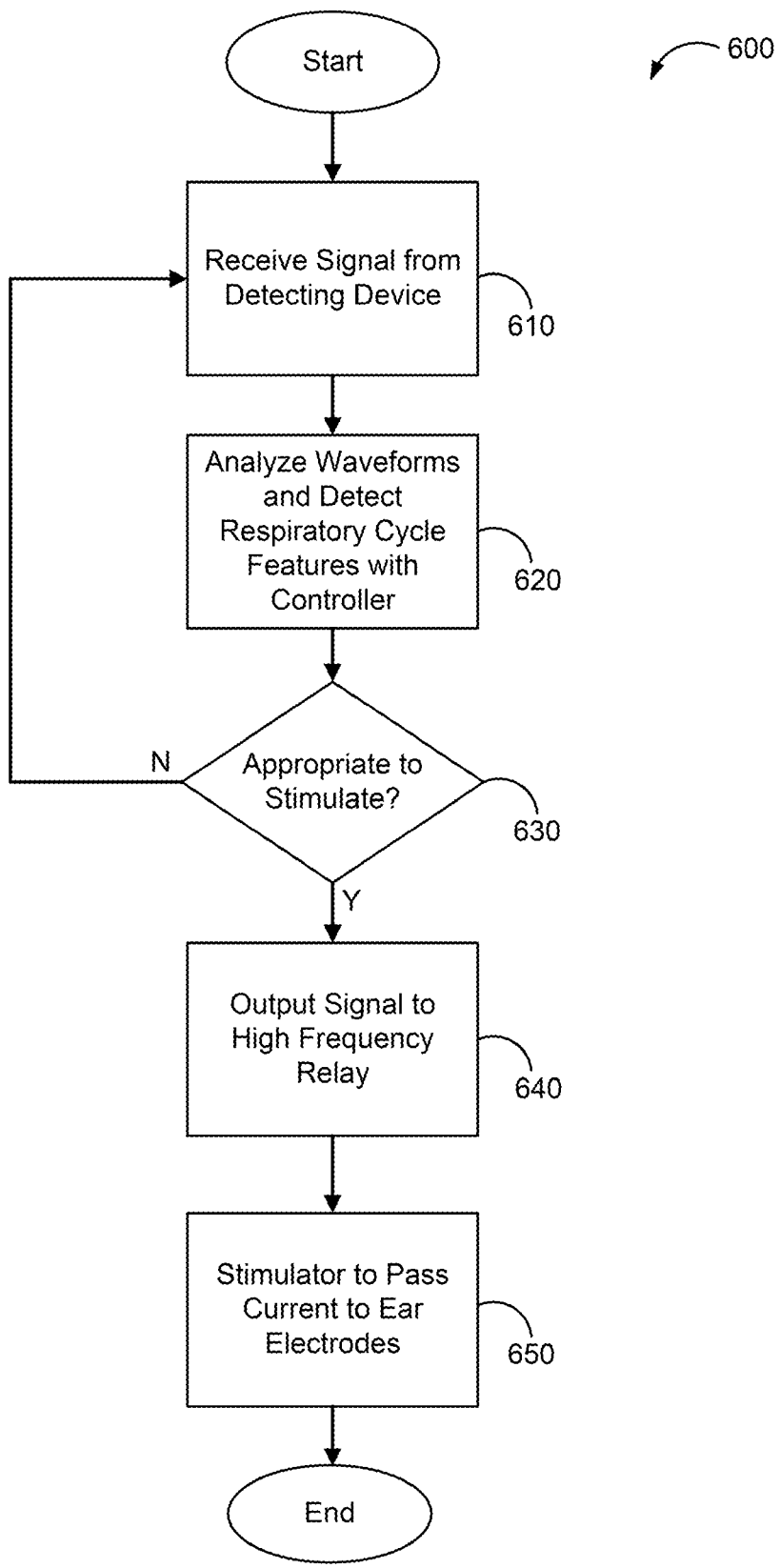
FIG. 6 is a flow chart setting forth some non-limiting example steps for a method performed using the respiration-gated neuromodulation apparatus of FIG. 3 to deliver neurostimulation to the vagus nerve of a patient, such as through an auricular branch of vagus nerve.

Referring to FIG. 6, a flow chart illustrates a method 600 to provide neurostimulation to the auricular nerve branch of the vagus nerve of a patient to treat hypertension, inflammatory disorders, or gastrointestinal disorders and the like. The detection device is connected to a transducer that converts the recorded electrical, electromechanical, or photovoltaic signals into a voltage signal. The transducer transmits this voltage signal to a controller at step 610. The controller analyzes the voltage signal in real-time and detects different features of the respiratory cycle of the individual at step 620. The controller may use an algorithm to perform an analysis of respiratory signals received from the detection device and determine the overall pulmonary activity of the individual. The controller identifies specific points on the respiratory signal where central autonomic nuclei may be more receptive to afferent input (i.e. during the expiration phase of the respiratory cycle) (see FIG. 5) and produce an output signal to the high-frequency relay and the stimulation circuit. Once these temporal landmarks are determined at step 630, the controller produces an output signal to a high-frequency relay or more directly causes stimulation to be performed at step 640. That is, the stimulator is caused to pass current to the electrodes at step 650. If the temporal landmarks are not identified at step 630 that would indicate stimulation is not appropriate, then the controller may wait until appropriate data is received from the detecting device.

In some configurations, the received signals may also be used to determine threshold values for each of expiration and inspiration in the respiratory cycle of the patient. An adaptive algorithm may calculate the respective thresholds for inspiration or expiration values based on a window of time. For example, a window of five respiratory cycles can be used to define each of the start-expiration threshold and the start-inspiration threshold. Moreover, as the window moves, the respective threshold values can be recalculated or updated. Other threshold values may also be algorithmically calculated, such as: mid-expiration or mid-inspiration threshold; maximum-lung volume threshold or minimum-lung volume threshold; or steepest slope in pulmonary activity for either of expiration or inspiration cycles, for example.

Figure 7:
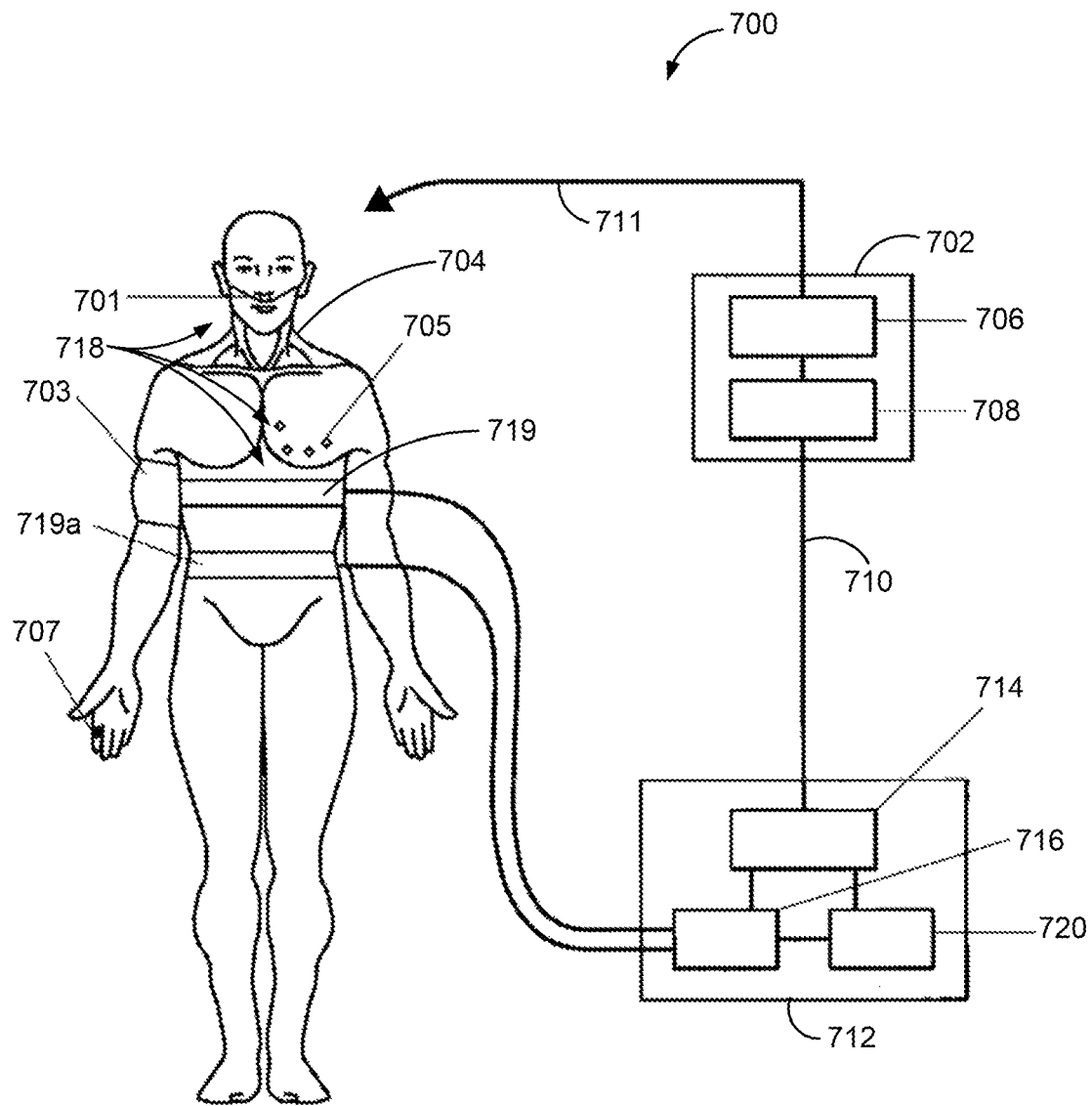
FIG. 7 is a schematic diagram of an apparatus for delivering an example neurostimulation regiment when deployed, as illustrated, on a patient.

Referring to FIG. 7, a system 700 for delivering neurostimulation to the cervical section of the vagus nerve of a patient through the use of respiratory-gated vagus nerve stimulation (RG-VNS) is depicted. In RG-VNS, the electrical stimulation of the vagus nerve may be simultaneously synchronized to the respiratory activity of the patient and varied based on the analysis of the respiratory activity of the patient. In one non-limiting configuration, the stimulation may be gated to specific phases of the respiratory cycle. For example, the vagus nerve may be stimulated during a specific phase of respiration, such as inspiration or expiration. In another implementation, a stimulation paradigm is gated to levels of carbon dioxide concentration, as measured non-invasively in the blood or expired air.

An example RG-VNS apparatus 700 includes a cervical branch-based device 702, a pulmonary-based device 712, and a link 710 between the cervical branch-based device 702 and the pulmonary-based device 712. The link 710 can be either wireless (e.g., radio-frequency, RF, Bluetooth) or a wired cable-link. It is to be appreciated that the apparatus may have other configurations. In some configurations, the system 700 is implanted including the ability to sense pulmonary activity (including respiratory activity) and provide vagus nerve stimulation. In other configurations, part of the system is implanted, such as the part for vagus nerve stimulation (cervical branch-based device 702) and part of the system is external, such as the part for sensing pulmonary activity (pulmonary-based device 712). For configurations where part of the system is implanted and part is external, the two parts may communicate with each other by wireless techniques (ultrasound, radio frequency, or light for example). In the case where the external part of the system is used to sense pulmonary activity, that information is communicated to the implanted part of the system to modulate vagus nerve stimulation.

In one configuration, the cervical branch-based device 702 includes at least one electrode 704, a stimulator circuit 706 connected to the electrode 704, and a power module 708 connected to the stimulator 706. The electrode 704 of the cervical branch-based device 702 is placed electrically near the vagus nerve of the patient and may be a percutaneous electrode that penetrates the skin, or a surface electrode that is placed on the skin or may be fully implanted in the patient. In some configurations, at least two electrodes 704 are used.

In one configuration, the electrode is a percutaneous electrode about 0.1-0.3 mm in diameter and about 2-5 mm in length. The electrode 704 may be manufactured from stainless steel or other conductive materials and may have a very fine tip. Alternatively, or in combination, one or more surface electrodes may be used. In one configuration, the surface electrodes may consist of a small disc (e.g., about 2-5 mm diameter) made from a conductive material (e.g., stainless steel) and attached to an adhesive band. Similarly, pre-gelled circular silver/silver chloride electrodes (about 5-10 mm diameter) can be used. It is to be appreciated that a variety of electrode configurations known to one of skill in the art may be used with the RG-VNS apparatus 700.

The present disclosure recognizes that respiration may be used to control VNS effects on cardiac regulation. The present disclosure recognizes that, during each respiratory cycle the heart rate slows during expiration and increases during inhalation, matching pulmonary blood flow to lung inflation and maintaining an appropriate oxygen diffusion gradient. This "respiratory sinus arrhythmia" (RSA) occurs by modulation of premotor cardiovagal neurons (e.g. NAmb) by diverse mechanisms, including afference (via NTS) from the lungs, as well as direct input from medullary respiratory neurons. Activation of excitatory 2nd-order neurons of the NTS during expiration increase premotor cardiovagal neuron firing rate and inhibit premotor sympathetic neurons. In contrast, during inhalation, activation of ventral respiratory group medullary neurons leads to increased inhibitory GABAergic and glycinergic synaptic transmission to premotor cardiovagal neurons. As the dorsal medullary vagal system operates in response to variations in respiratory volumes, neuromodulation of the vagus nerve during specific phases of the respiratory cycle where NTS may be more receptive to afferent input (i.e. during expiration) could optimize the effects of VNS on cardiovascular autonomic modulation.

A detection device 718 is adapted to detect pulmonary activity of the individual for delivery to the controller 714. The controller 714 is adapted to receive the detection signal and to generate an output signal for the stimulator 706 or effectuate operation of the stimulator 706. The stimulator 706 generates a neurostimulation signal that is delivered to the electrodes 704 based on control via the controller 714. It is to be appreciated that the electrode 704 may comprise a multi-contact electrode, e.g., a bipolar electrode. The electrode 704 can be connected to the stimulator 706 by a link 711, which may include insulated and shielded (e.g., radio frequency shielded) conductive leads. Alternatively, or in combination, the link 711 may be a wireless connection, such as through radio frequency transponders and receivers.

The detector 718 may include a respiratory belt 719 to detect respiratory movements. Other configurations are also possible. For example, the detector 718 may include a first respiratory belt 719 worn around the upper chest area and/or a second respiratory belt 719a worn around the abdominal area. If both the first and second respiratory belts 719, 719a are utilized, an algorithm may combine signals received from each of the respiratory belts to determine an overall respiratory activity of the patient. In another configuration, the detector 718 includes chest electrodes 705 located on the chest of a patient that may be adapted or combined with other methods to evaluate changes in electrical impedance across the thoracic region over the respiratory cycle to detect respiratory movement. The respiratory belt 719 may be equipped with a serial pneumatic bellow (where pressure inside the bellows may vary based on lung volume), a strain gage, or a piezoelectric device that is also in serial with the belt fabric, or a combination thereof.

The system may include pulse sensors 707 on the extremities to measure blood pressure in peripheral arteries and derive waveforms to calculate cardiac performance. A blood pressure cuff 703 or sphygmomanometer may also be used to measure blood pressure. In another configuration, the detection device will incorporate a nasal cannula 701 to evaluate pulmonary activity by measuring respiratory flow and continuous exhaled concentration of carbon dioxide. As previously mentioned with FIG. 4, a waveform signal describing the changes in carbon dioxide concentrations during the respiratory cycle may be collected. In another implementation, carbon dioxide detection will utilize an optical transcutaneous sampling cell for effective detection.

In some configurations, the stimulator 706 may be housed in an enclosure sized and configured to be implanted near the cervical branch of the vagus nerve of a patient. The stimulator 706 may take input from a controller 714 (e.g., a microchip and/or computer) on the pulmonary-based device 712. The stimulator 706 may output its signal to an electrode (e.g., either anode or cathode) 704 via insulated and shielded conductive leads, as described above, and receive the return signal via the return electrode.

The stimulator 706 may deliver various electrical signals to the vagus nerve using electrode 704. Once a trigger signal is generated from the controller 714, the stimulator 706 may deliver pulses. As a non-limiting example, the pulses may include a constant-current burst of bi-phasic square wave at a frequency of about 1-100 Hz (or higher frequencies including up to about 20 KHz in some configurations). As another non-limiting example the simulation may use current intensity in a range of 0.25 mA to 20 mA. Each pulse may have a pulse width varying from about 100-1000 microseconds. The burst timing of the burst may depend on the algorithm used to trigger the stimulation off of the pulmonary signal and whether the burst is a fixed duration, is a percentage of the measured respiratory rate, terminates at a detected phase of the respiratory cycle, or is based on some other algorithm implemented in the controller 714. For example, the burst may begin upon detection of the expiration phase of the respiratory signal and continue for 25% of the average measured respiratory interval. In one non-limiting implementation, the burst may begin once the stimulator 706 receives a trigger signal (e.g., Transistor-Transistor Logic or TTL) from the controller 714 on the pulmonary-based device 712.

The power module 708 may provide power (e.g., battery) to the stimulator 706. The power module 708 may be housed, but need not be housed, inside the same enclosure as the stimulator 706 and can be connected to the stimulator 706 with insulated leads known in the art. For example, the power module 708 may include a battery that can be rechargeable or the battery may be removed for recharging, depending on specifications and/or applications. The power module 708 may also include or comprise a non-rechargeable battery.

The pulmonary-based device 712 may include the controller 714, a transducer 716, the detector 718, and a power supply 720. As stated previously, it is to be appreciated that the RG-VNS may have other configurations. For example, the power module 708 and the power supply 720 may be in the same device, or may be the same device. Alternatively, or in combination, the stimulator 706 may be housed outside of the cervical branch-based device 702 such as inside the pulmonary-based device 712, for example. The cervical branch-based device 702 may have a pulmonary activity detector, such as when the nasal airflow detector is mechanically linked to a head piece that also houses a portion of the electrodes 704.

Use of the Above-Described RG-VNS System for the Treatment of Cardiovascular Diseases and Comorbid Mood Disorders RG-VNS may be used to treat a myriad of cardiovascular diseases. Given that afferent stimulation is supplied to the vagus nerve during select phases of the respiratory cycle, RG-VNS may enhance the effects of VNS on modulation of the cardiac autonomic nervous system. A chronic withdrawal of cardiac vagal tone is strongly associated with an increased risk of sudden death and arrhythmias. A hypoactive parasympathetic system is also considered a risk factor for decompensation and mortality in patients with heart failure and acute myocardial infarction. Autonomic nervous system dysfunction has also been linked to the pathogenesis of hypertension, and the development of resistance to treatment, structural cardiac remodeling and abnormal left ventricular function in this condition. Therefore, a therapeutic intervention oriented to enhance vagal control, such as RG-VNS, can improve cardiac autonomic balance and favorably affect the clinical condition of patients with hypertension, cardiac arrhythmias, coronary heart disease, acute myocardial infarction and heart failure.

The use of the above-described RG-VNS system can have a significant impact in the treatment of the comorbidity between major depression and cardiovascular disease. Over 350 million people worldwide live with major depressive disorder, which has been associated with a significantly increased cardiovascular risk and a higher rate of complications and new ischemic events in subjects with coronary heart disease. Depression is also related with a significant negative impact in the prognosis of patients with hypertension, heart failure, and atrial fibrillation. Autonomic dysfunction, consisting of increased sympathetic activity and reduced cardiac vagal tone, has been found to be one of the pathophysiological mechanisms causing this increased cardiovascular risk in major depression. Therefore, the use of RG-VNS to increase vagal cardiac regulation can significantly reduce the impact of this comorbidity. Furthermore, the optimized activation of NTS by RG-VNS can also modulate afferent projections to cortical areas involved in mood regulation, and subsequently reduce depressive symptomatology in these patients.

Use of the Above-Described RG-VNS System for the Treatment of Inflammation-Associated Disorders The vagus nerve is involved in the regulation of immune responses. The presence of cytokines such as IL-1 in the periphery activate receptors expressed by cells in parasympathetic ganglia, and this information is relayed via afferent vagal fibers to the NTS and the paraventricular nucleus (PVN) of the hypothalamus, which are major centers for neural-immune, hormonal and autonomic regulation. On the efferent side, the NTS provides glutamatergic innervation of premotor vagal neurons in the dorsal motor nucleus of the vagus (DMNX) and the NAmb. These are the sources of the efferent signals of organs associated with immune response including the liver and gastrointestinal system. In addition, acetylcholine release from the vagus nerve modulates inflammatory processes via alpha 7 nicotinic receptors that inhibit NF kappa B and cytokine synthesis and release. The modulation of brainstem autonomic nuclei and subsequently the activity of the cholinergic anti-inflammatory pathway by using RG-VNS can have implications for the treatment of inflammation-associated disorders such as sepsis, rheumatoid arthritis, systemic lupus erythematosus, ulcerative colitis, Crohn's disease, mood disorders, and asthma, as non-limiting examples.

Besides its effects on cardiovascular regulation, vagus nerve stimulation could also modulate neuroendocrine responses to stress. Experimental studies have reported that NTS plays a critical role in the mediation of neurosteroids effects on the modulation of the Hypothalamic-Pituitary-Adrenal and -gonadal (HPA and HPG) axes activity and inflammation. Upregulation of neurosteroids production in the NTS has been associated with attenuated Adrenocorticotropic Hormone (ACTH) and corticosterone release in stressed rats. In addition, NTS is an area with high concentration of estrogen receptors-β (ER-β) and previous studies have shown that the administration of ER-β agonists is associated with decreased synthesis of noradrenergic enzymes in the NTS and reduced HPA response to stress. Because of the important role of NTS on neuroendocrine regulation, the modulation of its activity by using vagus nerve stimulation could have implications for the treatment of disorders associated with chronic deficits in central neurosteroid production.

Use of the Above-Described RG-VNS System for the Treatment of Chronic Pain

Autonomic dysfunction has been linked with clinically-relevant parameters in chronic pain patients, and a number of studies have demonstrated that evoked pain stimuli induce increased sympathetic and/or decreased parasympathetic outflows. Autonomic premotor nuclei interact with pain-processing nuclei in the brainstem and higher brain nociceptive regions such as the periaqueductal gray and anterior cingulate cortex, possibly contributing to the central pathophysiological mechanisms responsible for altered nociception in chronic pain patients. An optimized modulation of medullary autonomic nuclei by using the above-described RG-VNS system can have significant analgesic effects of relevance for the treatment of chronic pain disorders such as migraine, fibromyalgia, trigeminal neuralgia, osteoarthritis, phantom limb pain, and low-back pain as non-limiting examples.

Use of the Above-Described RG-VNS System for the Treatment of Anxiety Disorders

Anxiety disorders are characterized by basal overactivation of the sympathetic nervous system. Multiple studies have shown that patients with anxiety disorders such as post-traumatic stress disorder, generalized anxiety disorder or panic disorder present high resting heart rate and blood pressure, increased plasma and urine catecholamine levels and decreased heart rate variability. These alterations in autonomic function contribute to an increased cardiovascular risk in a similar manner as reported for major depression. Moreover, an elevated sympathetic tone contributes to reinforcement of a hyperarousal state, and elicitation of fight/flight responses and avoidance behaviors in these patients. The optimized modulation of sympatho-vagal balance with the above-described RG-VNS system can be effective in reducing the psychological distress and functional impairment as well as diminishing the risk of cardiovascular comorbidity associated with anxiety disorders such as generalized anxiety disorder, social phobia, panic disorder, obsessive-compulsive disorder, post-traumatic stress disorder, and specific phobias as non-limiting examples.

Use of the Above-Described RG-VNS System for the Treatment of Disorders associated with Chronic Hypoxia/Hypercapnia Patients with conditions such as chronic pulmonary obstructive disease, sleep apnea, heart failure or morbid obesity experience repetitive hypoxaemic stress that leads to enhanced peripheral chemoreflex sensitivity and consequently high levels of sympathetic activity and cardiovascular dysregulation. In one implementation, the above-described RG-VNS system can incorporate capnography measurements to provide an indirect measurement of carbon dioxide partial pressure in the arterial blood. This signal is closely related to activation of arterial chemoreceptors in patients with hypoxemic disorders and may be used to trigger vagal stimulation in order to downregulate and increased sympathetic outflow.

The activity of the central autonomic nuclei is also modulated by the activation of peripheral chemoreceptors located in the carotid and aortic bodies. These receptors are activated by a fall in oxygen or a rise in carbon dioxide and send neural signals to the medulla that synapse in the NTS. This pathway subsequently affects the level of activity in sympathetic and parasympathetic efferent tracts, regulating cardiovascular function. The modulation of neural autonomic signaling in response to chemoreceptor activation could have important implications for the cardiovascular regulation of several cardiovascular disorders associated with hypoxia, hypercapnia and acidemia.

Use of RG-VNS for the Treatment of Primary Autonomic System Disorders

Primary autonomic disorders such as postural orthostatic tachycardia syndrome and neurocardiogenic syncope are characterized by exaggerated sympathoexcitation responses, followed by vagal overcoming of cardiovascular activity leading to low cerebral perfusion, transient loss of consciousness and postural tone. The above-described RG-VNS system can be used for optimized modulation of medullary autonomic nuclei activity and regulation of cardiovascular sympatho-vagal responses in these disorders.

Figure 8:
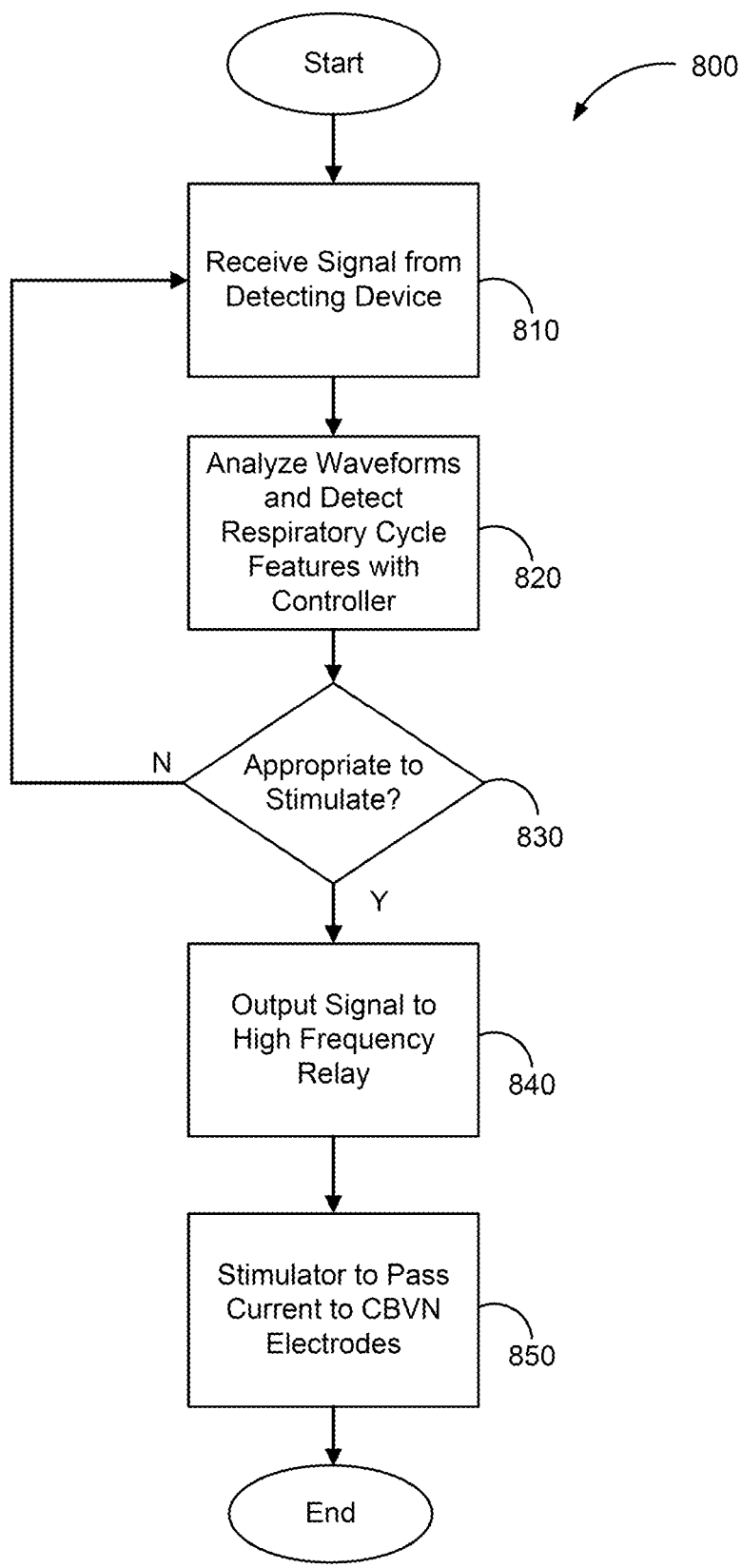
FIG. 8 is a flowchart setting forth some non-limiting example steps of a method performed using the apparatus of FIG. 7 to deliver neurostimulation to the vagus nerve of a patient, such as through a cervical branch of the vagus nerve.

Referring to FIG. 8, a flow chart is provided illustrating non-limiting steps of a method 800 to provide neurostimulation to the cervical branch of the vagus nerve of a patient. Such may be used, for example, to treat epilepsy, cardiovascular disease, comorbid mood disorders, inflammation-associated disorders, chronic pain, anxiety disorders, disorders associated with chronic hypoxia/hypercapnia, primary autonomic system disorders, and the like. The detection device is connected to a transducer that will convert the recorded electrical, electromechanical, or photovoltaic signals into a voltage signal. The transducer will transmit this voltage signal to a controller at step 810. The controller analyzes the voltage signal in real-time or near-real-time and will detect different features of the respiratory cycle of the individual at step 820. The controller may use an algorithm to perform an analysis of respiratory signals received from the detection device and determine the overall pulmonary activity of the individual. The controller identifies specific points on the respiratory signal where central autonomic nuclei may be more receptive to afferent input (i.e. during the expiration phase of the respiratory cycle) (see FIG. 5). Once these temporal landmarks are determined at step 830, the controller produces an output signal delivered to a high-frequency relay or directly causes the stimulator to act at step 840. The stimulator passes current to the cervical vagus electrodes at step 850. If the temporal landmarks are not identified at step 830, that would indicate stimulation is not appropriate and the controller may wait until appropriate data is received from the detecting device, or may deliver the stimulation signal asynchronously.

In some configurations, the received signals may also be used to determine threshold values for each of expiration and inspiration in the respiratory cycle of the patient. An adaptive algorithm may calculate the respective thresholds for inspiration or expiration values based on a window of time (e.g., the previous five breaths). For example, a window can be used to define each of the start-expiration threshold and the start-inspiration threshold. Moreover, as the window moves, the respective threshold values can be recalculated or updated. Other threshold values may also be algorithmically calculated, such as: mid-expiration or mid-inspiration threshold; maximum-lung volume threshold or minimum-lung volume threshold; or steepest slope in pulmonary activity for either of expiration or inspiration cycles, for example.

Figure 9:
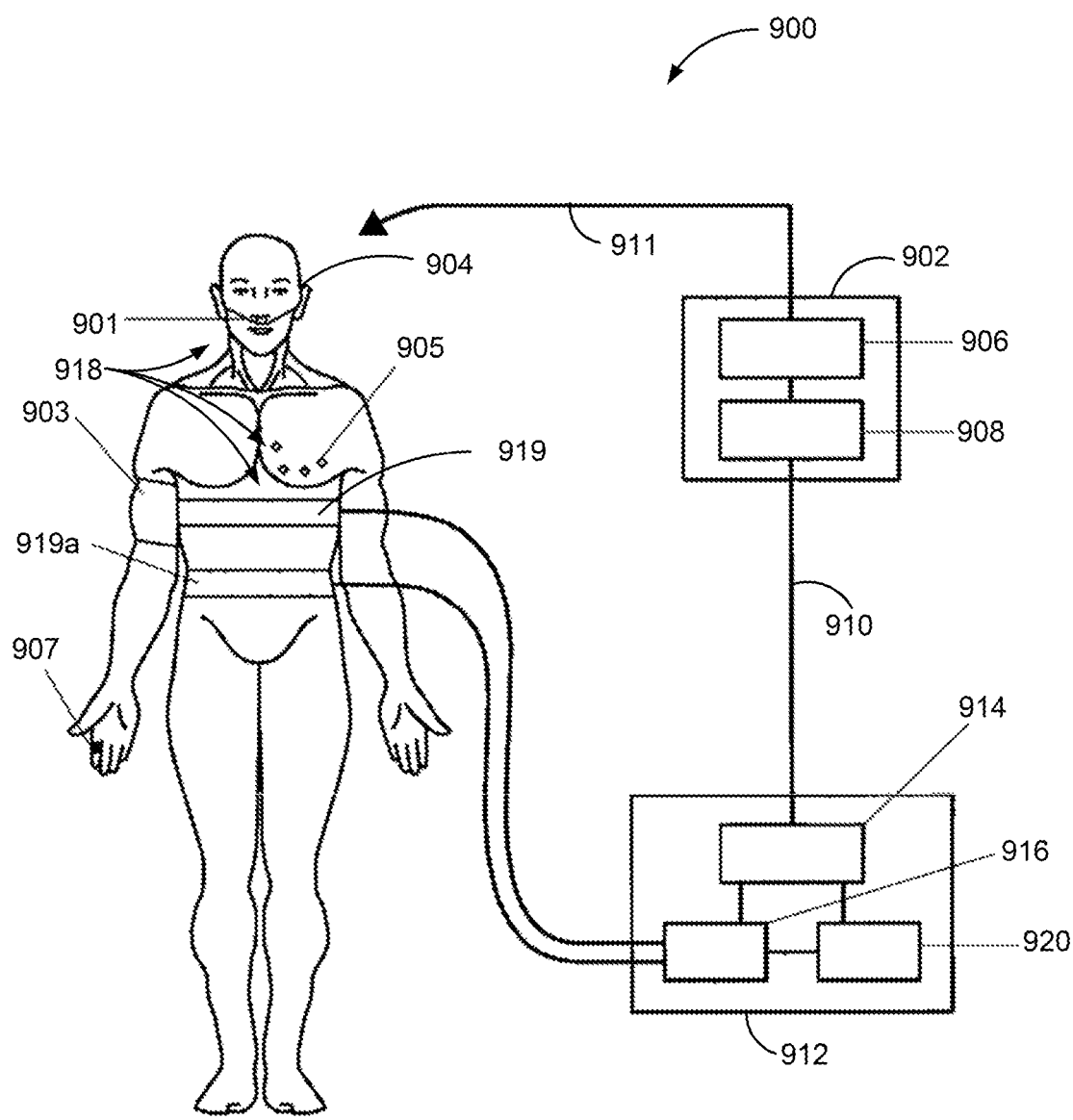
FIG. 9 is a schematic diagram of an apparatus for delivering an example neurostimulation regiment when deployed, as illustrated, on a patient.

Referring to FIG. 9, a system for spinal cord stimulation (SCS) 900 for delivering neurostimulation to the spinal cord of a patient to provide therapeutic outcome with signals that are adjusted based on pulmonary activity is depicted. In respiratory-gated spinal cord stimulation (RG-SCS), the electrical stimulation of the spinal cord may be simultaneously synchronized to the pulmonary activity of the patient and varied based on the analysis of the pulmonary activity of the patient. In one configuration, the stimulation is gated to specific phases of the respiratory cycle. For example, the RG-SCS may be stimulated during a specific phase of respiration, such as inspiration or expiration. In another implementation, a stimulation paradigm is gated to levels of carbon dioxide concentration, as measured non-invasively in the blood or expired air.

The example RG-SCS apparatus 900 includes a spinal cord-based device 902, a pulmonary-based device 912, and a link 910 between the spinal cord-based device 902 and the pulmonary-based device 912. The link 910 can be either wireless (e.g., radio-frequency, RF, Bluetooth) or a wired cable-link. It is to be appreciated that the apparatus may have other configurations. In some configurations, the entire system 900 may be implanted including the ability to sense pulmonary activity (including respiratory activity, using impedance plethysmography for example) and provide spinal cord stimulation. In other embodiments part of the system is implanted, such as the part for spinal cord stimulation (spinal cord-based device 902) and part of the system is external, such as the part for sensing pulmonary activity (pulmonary-based device 912). For configurations where part of the system is implanted, and part is external, the two parts may communicate with each other by wireless techniques (ultrasound, radio frequency, or light for example). In the case where the external part of the system is used to sense pulmonary activity, that information is communicated to the implanted part of the system to modulate spinal cord stimulation.

In one configurations, the spinal cord-based device 902 can include at least one electrode 904, a stimulator circuit 906 connected to the electrode 904, and a power module 908 connected to the stimulator 906. The electrode 904 of the spinal cord-based device 902 is placed electrically near the spinal cord of the patient to stimulate. In non-limiting examples, the electrode 904 is placed in electrical contact with the dorsal nerve fibers of the spinal cord or the dorsal root ganglia. The electrode 904 may be a percutaneous electrode that penetrates the skin, or a surface electrode that placed on the skin or may be fully implanted in the patient with the electrodes in the epidural space within the spinal column. In some configurations, at least two electrodes 904 are used. In one configuration, the electrode is a percutaneous electrode about 0.1-0.3 mm in diameter and about 2-5 mm in length. The electrode 904 may be manufactured from platinum, stainless steel or other conductive materials and may have a very fine tip for the percutaneous embodiment.

Alternatively, or in combination, one or more surface electrodes may be used. In one configuration, the surface electrodes may consist of a small disc (e.g., about 2-5 mm diameter) made from a conductive material (e.g., stainless steel or conductive rubber) and attached to an adhesive band. Similarly, pre-gelled circular silver/silver chloride electrodes (about 5-10 mm diameter) can be used. It is to be appreciated that a variety of electrode configurations known to one of skill in the art may be used with the RG-SCS apparatus 900.

Respiration may be an important parameter for improving the benefits of SCS. During each respiratory cycle the heart rate slows during expiration and increases during inhalation, matching pulmonary blood flow to lung inflation and maintaining an appropriate oxygen diffusion gradient. This "respiratory sinus arrhythmia" (RSA) occurs by modulation of premotor cardiovagal neurons (e.g. NAmb) by diverse mechanisms, including afference (via NTS) from the lungs, as well as direct input from medullary respiratory neurons. Activation of excitatory 2nd-order neurons of the NTS during expiration increase premotor cardiovagal neuron firing rate and inhibit premotor sympathetic neurons. In contrast, during inhalation, activation of ventral respiratory group medullary neurons leads to increased inhibitory GABAergic synaptic transmission to premotor cardiovagal neurons. The regulatory role of NTS on premotor cardiovagal neurons is also affected by changes in cardiac output. During the systolic phase of the cardiac cycle, ejection of blood from the left ventricle induces a sudden increase in mean arterial pressure and activation of baroreceptors located in the walls of the carotid artery sinus and aortic arch. This afferent neural feedback is relayed to NTS, which subsequently activates, via glutamatergic pathway, NMDA and non-NMDA receptors on the NAmb, and results in increased efferent parasympathetic signaling to the sino-atrial (SA) and atrio-ventricular (AV) nodes.

A detection device 918 is adapted to detect pulmonary activity of the individual and convert the detected activity into a corresponding detection signal for delivery to the controller 914. The controller 914 is adapted to receive the detection signal and to generate an output signal for the stimulator 906. The stimulator 906 is adapted to receive the output signal and to generate a neurostimulation signal to the electrodes 904. It is to be appreciated that the electrode 904 may comprise a multi-contact electrode, e.g., a bipolar electrode. The electrode 904 can be connected to the stimulator 906 by a link 911, which may include insulated and shielded (e.g., radio frequency shielded) conductive leads. Alternatively, or in combination, the link 911 may be a wireless connection, such as through radio frequency transponders and receivers.

The detector 918 may include a respiratory belt 919 to detect respiratory movements. Other configurations are also possible. For example, the detector 918 may be a first respiratory belt 919 worn around the upper chest area and/or a second respiratory belt 919a worn around the abdominal area. If both the first and second respiratory belts 919, 919a are utilized, an algorithm may combine signals received from each of the respiratory belts to determine an overall respiratory activity of the patient. In another configuration, the pulmonary activity detector includes chest electrodes 905 located on the chest of a patient that may be adapted or combined with other methods to evaluate changes in electrical impedance across the thoracic region over the respiratory cycle to detect respiratory movement. The system may include pulse sensors 907 on the extremities to measure blood pressure in peripheral arteries and derive waveforms to calculate cardiac performance. A blood pressure cuff 903 or sphygmomanometer may also be used to measure blood pressure. In another configuration, the detection device will incorporate a nasal cannula 901 to evaluate pulmonary activity by measuring respiratory flow and continuous exhaled concentration of carbon dioxide. As previously mentioned with respect to FIG. 4, a waveform signal describing the changes in carbon dioxide concentrations during the respiratory cycle may be collected. In another implementation, carbon dioxide detection will utilize an optical transcutaneous sampling cell for effective detection.

In some configurations, the stimulator 906 may be housed in an enclosure sized and configured to be implanted near the spinal cord of a patient. The stimulator 906 may take input from a controller 914 (e.g., a microchip and/or computer) on the pulmonary-based device 912. The stimulator 906 may output its signal to an electrode (e.g., either anode or cathode) 904 via insulated and shielded conductive leads, as described above, and receive the return signal via the return electrode.

The stimulator 906 may deliver various electrical signals to the spinal cord using electrode 904. Once a trigger signal is generated from the controller 914, the stimulator 906 may deliver a burst of pulses. The burst timing of the burst will depend on the algorithm used to trigger the stimulation off of the pulmonary signal and whether the burst is a fixed duration, is a percentage of the measured respiratory rate, terminates at a detected phase of the respiratory cycle, or is based on some other algorithm implemented in the controller 914. For example, the burst may begin upon detection of the expiration phase of the respiratory signal and continue for 25% of the average measured respiratory interval. In one implementation, the burst may begin once the stimulator 906 receives a trigger signal (e.g., Transistor-Transistor Logic or TTL) from the controller 914 on the pulmonary-based device 912.

The power module 908 may provide power (e.g., battery) to the stimulator 906. The power module 908 may be housed, but need not be housed, inside the same enclosure as the stimulator 906 and can be connected to the stimulator 906 with insulated leads known in the art. For example, the power module 908 may include a battery that can be rechargeable or the battery may be removed for recharging, depending on specifications and/or applications. The power module 908 may also include or comprise a non-rechargeable battery.

The pulmonary-based device 912 may include the controller 914, a transducer 916, a detector 918. gage or a nasal air flow detector), and a power supply 920. The transducer 916 may be any electrical, electro-mechanical, photovoltaic or other device that converts one type of energy to another. For example, the transducer 916 may convert either strain (from a strain gage), or air pressure (from bellows or from a nasal air flow detector) into a voltage signal. In one implementation, it may be included with and rest inside an enclosure on the respiratory belt 919, which may also contain the controller 914 or the power supply 920.

The controller 914 may be any device, which includes a computer readable medium including code that, when executed by a processor, performs logical steps. The controller 914 may include circuitry capable of analyzing waveforms, generating a trigger for the stimulator 906, or a microchip with embedded software, as non-limiting examples.

As stated previously, it is to be appreciated that the RG-SCS may have other configurations. For example, the power module 908 and the power supply 920 may be in the same device, or may be the same device. Alternatively, or in combination, the stimulator 906 may be housed outside of the spinal cord-based device 902 such as inside the pulmonary-based device 912, for example. The spinal cord-based device 902 may have a pulmonary activity detector, such as when the nasal airflow detector is mechanically linked to a head apparatus that also houses a portion of the electrodes 904.

Use of the Above-Described RG-SCS System for the Treatment of Cardiovascular Diseases Disorders RG-SCS may be used to improve the treatment of cardiovascular diseases. SCS is currently used to treat angina, and experimental work in heart failure has shown promise but inconsistent results. The proposed mechanism of benefit by SCS is reduced cardiac sympathetic activity and concomitant increased parasympathetic activity. The above-described RG-SCS system may enhance the effects of SCS on modulation of the cardiac autonomic nervous system by supplying stimulation to the spinal cord during select phases of the respiratory cycle. As the dorsal medullary vagal system operates in response to variations in cardiac output and respiratory volumes, neuromodulation of the SCS during specific phases of the cardiac and respiratory cycles where NTS may be more receptive to afferent input (i.e. during expiration) could improve the effects of SCS.

The activity of the central autonomic nuclei is also modulated by the activation of peripheral chemoreceptors located in the carotid and aortic bodies. These receptors are activated by a fall in oxygen or a rise in carbon dioxide and send neural signals to the medulla that synapse in the NTS. This pathway subsequently affects the level of activity in sympathetic and parasympathetic efferent tracts, regulating cardiovascular function. The modulation of neural autonomic signaling in response to chemoreceptor activation can have important implications for the treatment of angina.

Use of the Above-Described RG-SCS System for the Treatment of Chronic Pain

Historically, the primary application of SCS is in the treatment of back and limb pain. While much success has been achieved, there are opportunities to improve the durability of the therapy and the consistency of clinical benefit. Aspects of long-term SCS pain relief are associated with autonomic responses, and RG-SCS can enhance those clinical benefits. Administration of RG-SCS could significantly modulate NTS activity and consequently improve the antinociceptive effects of SCS. NTS is a key relay station that transfers information and regulates the activity of monoamine nuclei in the brainstem such as locus coeruleus (noradrenergic) and raphe (serotonergic) nuclei, structures that play an important role in anti-nociceptive processing. Importantly, relief of chronic pain by SCS may result from induced release of serotonin and norepinephrine originating from pathways descending from these nuclei into the dorsal horn, resulting in modulation of spinal neuronal activity.

Figure 10:
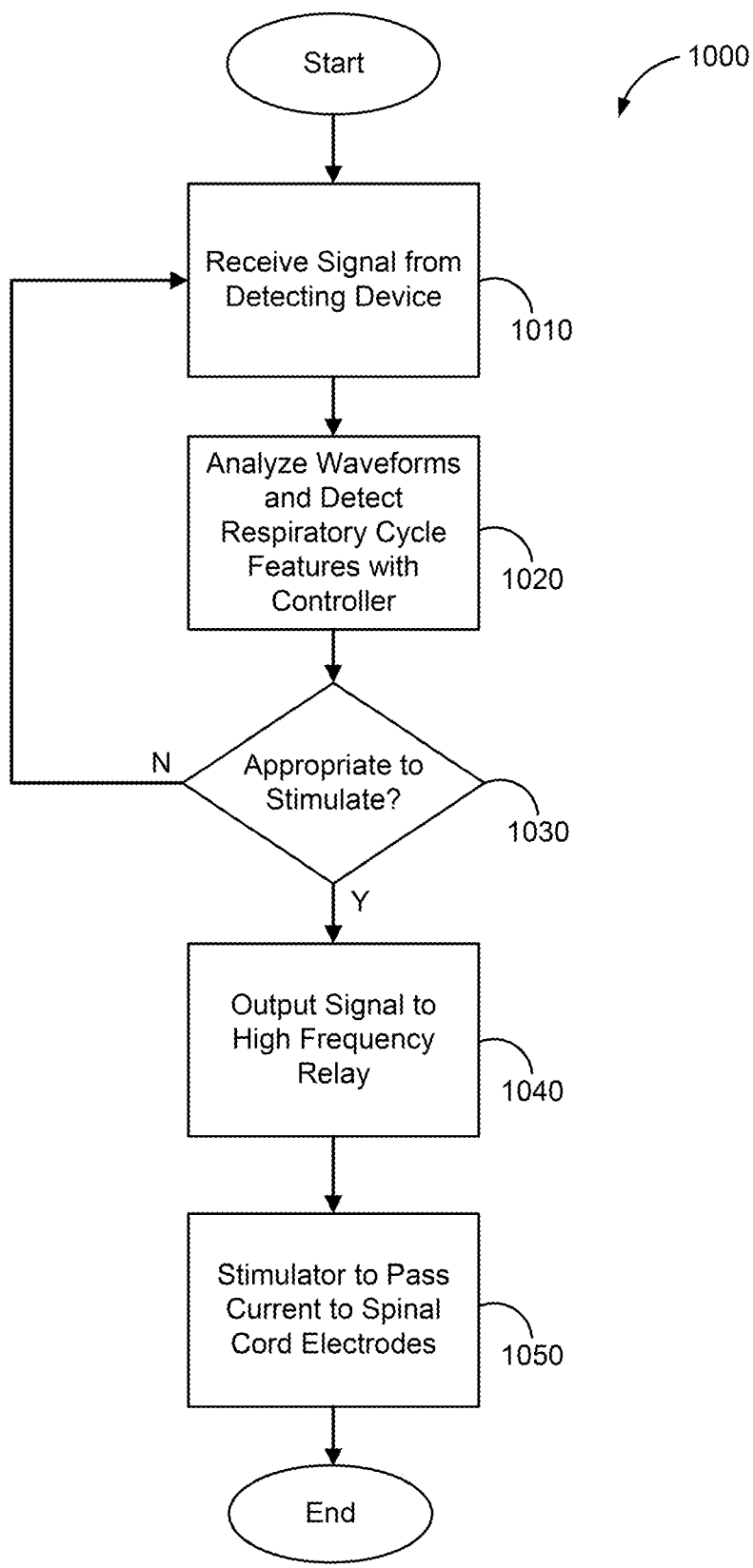
FIG. 10 is a flowchart setting forth some non-limiting example steps of a method performed using the apparatus of FIG. 9 to deliver neurostimulation to a portion of a patient, such as a spinal cord.

Referring to FIG. 10, a flow chart illustrates a method 900 to provide neurostimulation to the spinal cord of a patient to treat back and limb pain, angina, cardiovascular disease disorders, chronic pain, and the like. The detection device is connected to a transducer that converts the recorded electrical, electromechanical, or photovoltaic signals into a voltage signal. The transducer transmits this voltage signal to a controller at step 1010 to analyze waveforms. The controller analyzes the voltage signal in real-time or near real-time and detects different features of the respiratory cycle of the individual at step 1020. The controller may use an algorithm to perform an analysis of respiratory signals received from the detection device and determine the overall pulmonary activity of the individual. The controller identifies specific points on the respiratory signal where central autonomic nuclei may be more receptive to afferent input (i.e. during the expiration phase of the respiratory cycle) (see FIG. 5) and produces an output signal to the high-frequency relay and the stimulation circuit. Once these temporal landmarks are determined at step 1030, the controller produces an output signal to a high-frequency relay at step 1040. The high-frequency relay may then allow the stimulator to pass current to the ear electrodes at step 1050. If the temporal landmarks are not identified at step 1030 that would indicate stimulation is not appropriate, and the controller may wait until appropriate data is received from the detecting device.

In some configurations, the received signals may also be used to determine threshold values for each of expiration and inspiration in the respiratory cycle of the patient. An adaptive algorithm may calculate the respective thresholds for inspiration or expiration values based on a window of time (e.g., the previous five breaths). For example, a window of five respiratory cycles can be used to define each of the start-expiration threshold and the start-inspiration threshold. Moreover, as the window of five breaths moves, the respective threshold values can be recalculated or updated. Other threshold values may also be algorithmically calculated, such as: mid-expiration or mid-inspiration threshold; maximum-lung volume threshold or minimum-lung volume threshold; or steepest slope in pulmonary activity for either of expiration or inspiration cycles, for example.

The present disclosure has described one or more preferred embodiments, and it should be appreciated that many equivalents, alternatives, variations, and modifications, aside from those expressly stated, are possible and within the scope of the invention.

The invention claimed is:

1. An apparatus comprising:
    an electrode configured to be electrically coupled to an afferent nerve fiber of a vagus nerve of a subject;
    a stimulation circuit connected to the electrode to deliver a stimulation signal to the electrode, thereby stimulating the afferent nerve fiber;
    at least one processor configured to:
        determine one or more pulmonary characteristics of the subject, the one or more pulmonary characteristics including a concentration of carbon dioxide; and
        deliver the stimulation signal to the stimulation circuit to effectuate electrical stimulation of the subject based on the concentration of carbon dioxide.

2. The apparatus of claim 1 wherein the one or more pulmonary characteristics include at least one of inspiration and expiration and wherein delivering the stimulation signal includes timing a delivery of stimulations to the subject at a beginning of expiration and extending through a portion of expiration.

3. The apparatus of claim 2 wherein the processor is configured to terminate delivery of stimulations to the subject prior to inspiration.

4. The apparatus of claim 1 wherein the processor is configured to utilize an adaptive window to determine a timing of the pulmonary characteristic.

5. The apparatus of claim 1 further comprising a detector configured to monitor pulmonary activity of the subject and communicate a pulmonary activity waveform to the processor.

6. The apparatus of claim 5 wherein the detector includes at least one of a pulse sensor configured to measure blood pressure, a nasal cannula configured to measure respiratory flow or the concentration of carbon dioxide, or a respiration belt configured to measure expansion and contraction of a thorax of the subject during respiration.

7. The apparatus of claim 1 wherein the electrical stimulation is configured to achieve a therapeutic function to treat at least one of hypertension, inflammatory disorders, or gastrointestinal disorders.

8. The apparatus of claim 1 wherein the electrical stimulation includes at least one of:
    a constant-current pulse;
    a burst of bi-phasic square wave pulses;
    a frequency between 1-100 Hz;
    current intensity between 0.25 mA to 20 mA; and
    a pulse width between 100-1000 microseconds.

* * * * *